(12) United States Patent  (10) Patent No.: US 9,279,366 B1
Shields et al.  (45) Date of Patent: Mar. 8, 2016

(54) STEAM POWERED ENGINE

(75) Inventors: Stephen W. Shields, Hattiesburg, MS (US); David William Shields, Hattiesburg, MS (US)

(73) Assignee: SPINDYNE LLC, Hattiesburg, MS (US)

( * ) Notice: Subject to any disclaimer, the term of this patent is extended or adjusted under 35 U.S.C. 154(b) by 365 days.

(21) Appl. No.: 13/397,574

(22) Filed: Feb. 15, 2012

Related U.S. Application Data

(60) Provisional application No. 61/443,069, filed on Feb. 17, 2011.

(51) Int. Cl.
 *F02B 53/00* (2006.01)
 *F02C 5/00* (2006.01)
 *F01C 1/344* (2006.01)

(52) U.S. Cl.
 CPC .................. *F02C 5/00* (2013.01); *F01C 1/3441* (2013.01)

(58) Field of Classification Search
 USPC .................. 123/241, 200; 418/92, 90, 89, 45; 60/682, 659, 227; 335/258
 See application file for complete search history.

(56) References Cited

U.S. PATENT DOCUMENTS

| | | | |
|---|---|---|---|
| 2,786,421 A * | 3/1957 | Prendergast | ................... 418/248 |
| 3,040,530 A | 6/1962 | Yalnizyan | |
| 3,597,132 A | 8/1971 | Stahmer | |
| 3,890,071 A | 6/1975 | OBrien | |
| 3,988,082 A | 10/1976 | Rogers | |
| 4,047,856 A | 9/1977 | Hoffman | |
| 4,115,045 A * | 9/1978 | Wyman | ........................... 418/97 |
| 4,150,351 A * | 4/1979 | Berg | .............................. 335/258 |
| 4,204,817 A | 5/1980 | Kervagoret | |
| 4,451,219 A | 5/1984 | Kurherr | |
| 4,562,802 A * | 1/1986 | Groeger | ........................ 123/200 |
| 4,599,059 A * | 7/1986 | Hsu | ................................ 418/236 |
| 5,073,097 A | 12/1991 | Pipalov | |
| 5,165,238 A * | 11/1992 | Paul et al. | ........................ 60/682 |
| 5,235,945 A | 8/1993 | Testea | |
| 5,305,721 A * | 4/1994 | Burtis | ............................ 123/205 |
| 5,492,051 A * | 2/1996 | Schiffler et al. | .................. 92/125 |
| 5,579,733 A | 12/1996 | Tour | |
| 5,713,732 A | 2/1998 | Riney | |
| 5,758,617 A | 6/1998 | Saito | |
| 6,176,695 B1 | 1/2001 | Dye | |
| 6,530,357 B1 | 3/2003 | Yaroshenko | |
| 6,550,442 B2 | 4/2003 | Garcia | |
| 6,659,065 B1 | 12/2003 | Renegar | |

(Continued)

*Primary Examiner* — Jesse Bogue
*Assistant Examiner* — Thomas Olszewski
(74) *Attorney, Agent, or Firm* — Hall Estill Attorney at Law

(57) ABSTRACT

A rotary engine and method having a housing with a bore defining a cavity. A rotatable rotor in the cavity has a plurality of protuberant lobes with respective distal ends moving along the bore. Each of a plurality of vanes has a distal end biased to engage a perimeter of the rotor. The rotor rotates between neutral rotor positions where all of the lobes are simultaneously rotationally aligned with the vanes, and a plurality of different power stroke rotor positions between consecutive neutral rotor positions incrementally increasing in size a like plurality of volumetrically equivalent working fluid expansion chambers that are each in fluid communication with a respective working fluid inlet intersecting the bore and, in turn, incrementally decreasing in size a like plurality of volumetrically equivalent working fluid exhaust chambers each in continuous fluid communication with a respective working fluid outlet intersecting the bore.

16 Claims, 20 Drawing Sheets

(56) References Cited

U.S. PATENT DOCUMENTS

| | | |
|---|---|---|
| 6,681,738 B2 | 1/2004 | Endoh |
| 7,226,281 B2 | 6/2007 | Kato |
| 7,438,543 B2 | 10/2008 | Beez |
| 7,578,278 B2 | 8/2009 | Peitzke et al. |
| 7,713,042 B1 | 5/2010 | Rodgers |
| 7,845,332 B2 | 12/2010 | Wang |
| 8,424,284 B2 * | 4/2013 | Staffend et al. ............. 60/39.6 |
| 2002/0007815 A1 * | 1/2002 | Oh et al. .................... 123/236 |
| 2004/0255898 A1 | 12/2004 | Demafiles |
| 2005/0132703 A1 | 6/2005 | Matsumoto |
| 2009/0272094 A1 | 11/2009 | Zink |

\* cited by examiner

STEAM POWERED ENGINE

RELATED APPLICATION

This application claims the benefit of the earlier filing date of U.S. Provisional Patent Application Ser. No. 61/443,869.

FIELD

The present embodiments relate generally to devices and methods embodying an external combustion pistonless engine and more particularly without limitation to a rotary steam engine and use thereof.

SUMMARY

In some embodiments a rotary engine is provided having a housing with a bore defining a cavity. A rotatable rotor in the cavity has a plurality of protuberant lobes, each lobe having a distal end operably moving arcuately along the bore. Each of a plurality of vanes has a distal end biased to operably engage a perimeter of the rotatable rotor, the distal end extending from a portion of the vane operably reciprocating through the bore. The rotor operably rotates between neutral rotor positions and a plurality of different power stroke rotor positions between consecutive neutral rotor positions. In the neutral rotor positions all of the lobes are simultaneously rotationally aligned with the vanes. In the power stroke rotor positions there are incrementally increasing in size a like plurality of volumetrically equivalent working fluid expansion chambers that are each in fluid communication with a respective working fluid inlet intersecting the bore and, in turn, incrementally decreasing in size a like plurality of volumetrically equivalent working fluid exhaust chambers each in continuous fluid communication with a respective working fluid outlet intersecting the bore. At least some of the power stroke rotor positions define an exhaust chamber characterized by the rotor perimeter surface retracting each vane toward the bore downstream, in relation to rotor direction, of the respective working fluid outlet, simultaneously as the distal end of the adjacent upstream lobe moves along the bore upstream of the respective working fluid outlet.

In some embodiments a rotary engine is provided having a first rotor fixed in rotation with a rotatable shaft. The first rotor has a plurality of protuberant first lobes that are alignable at a first rotational position of the rotatable shaft with a like plurality of first vanes, each vane being biased to urge a distal end against the first rotor during rotation. The rotary engine also has a second rotor fixed in rotation with the rotatable shaft. The second rotor has a plurality of protuberant second lobes that are alignable at a different second rotational position of the rotatable shaft with a like plurality of second vanes, each vane being biased to urge a distal end against the second rotor during rotation. The rotary engine further has a fluid handling arrangement that independently drives the first and second rotors via a working fluid.

In some embodiments a method is provided that includes: obtaining a rotary engine having a housing defining a bore, a rotor having a plurality of protuberant lobes that are rotatable against the bore, and a plurality of vanes each biased against the rotor as the rotor rotates between neutral rotor positions where each of the plurality of lobes is aligned with a respective vane and a range of power stroke rotor positions between consecutive neutral positions; injecting a high energy fluid to expand against each of the lobes exerting substantially equivalent torques during an interval ending when the rotor is at a predetermined power stroke rotor position; and exhausting a comparatively low energy fluid downstream, in relation to rotor direction, of each of the lobes as each respective lobe rotates from one neutral rotor position to a plurality of power stroke rotor positions where the rotor perimeter surface retracts each vane toward the bore downstream of a respective working fluid outlet simultaneously as the distal end of the adjacent upstream lobe moves along the bore upstream of the respective working fluid outlet.

BACKGROUND

For purposes of this description and meaning of the claimed invention the present rotary engine embodiments are broadly directed to pistonless rotary engines. That is, the claimed embodiments are directed to an engine and associated methodology that converts the high energy state of a working fluid into rotating output motion, as distinguishable from the reciprocating output motion of a piston rotary engine.

Some types of such rotary engines are powered by internally combusting a fuel to set the rotor in motion by sequentially timed explosions resulting from the combustion. The Wankel engine is a well known type of such a rotary internal combustion engine, popularly commercialized by Mazda, for example, in the automotive industry. The Wankel engine, first patented in 1929, employs a rotor shaped similar to a Reuleaux triangle rotationally engaging an epitrochoid-shaped bore. Although the Wankel engine design requires less complexity and fewer precision moving parts than a comparative in-line or V configuration piston engine, it yet remains more complicated than present embodiments that advantageously remove the combustion process from within the engine. A four stroke internal combustion rotary engine, for example, requires that the rotor establish four separate chambers for supporting the combustion process; the intake chamber, the compression chamber, the combustion chamber, and the exhaust chamber. Further, the by-products of the combustion process inside such an engine can contaminate the engine internal working surfaces and thus be detrimental to achieving a reliably robust engine design.

Steam powered engines, on the other hand, are external combustion engines that generally receive high energy steam from a companion device, such as a package boiler and the like, and harness it in a manner that converts the input fluid energy into mechanical motion. Steam driven turbines, for example, are the predominant source of electrical power generation in the United States.

At the turn of the $20^{th}$ century there was a significant effort in the industry to marry the advantages of steam power to the advantages of the pistonless rotary engine design. A good number of what appeared to be promising solutions, such as the Hult engine, the Tower engine, and the Dolgorouki engine, all fell by the wayside to become no more than interesting museum artifacts. Improvements have eluded those skilled in the art for more than a century, preventing any breakthrough to a commercially viable design for a pistonless rotary steam engine. It is to those enabling improvements that the embodiments of the present invention are so directed.

DRAWINGS

Figure 13:
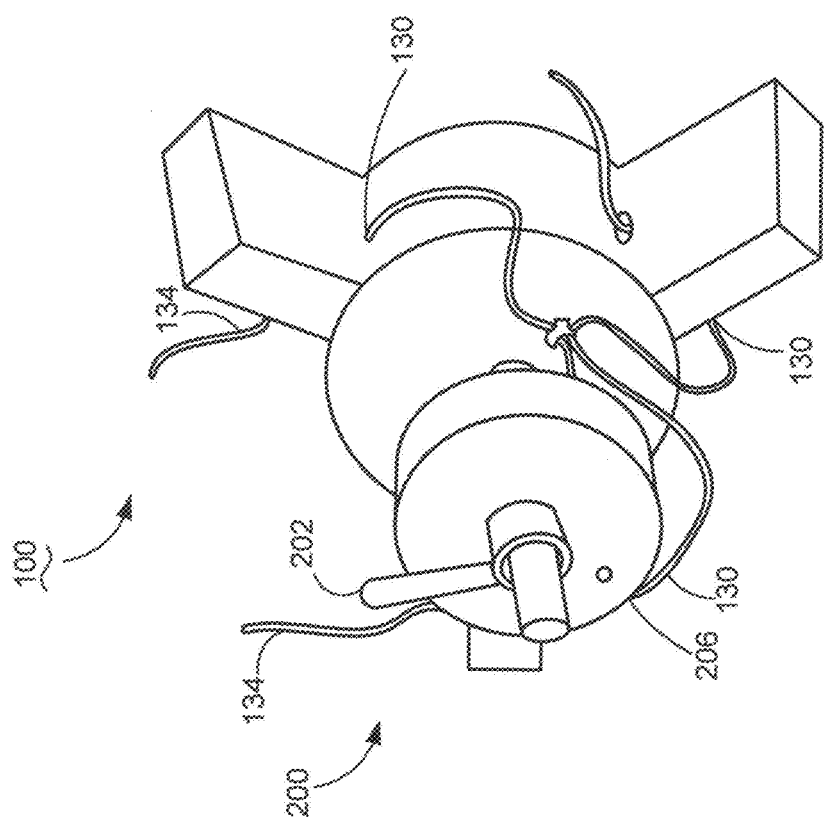
FIG. 13 is an isometric depiction similar to FIG. 1 but further showing a duration valve constructed in accordance with embodiments of the present invention.
Figure 15:
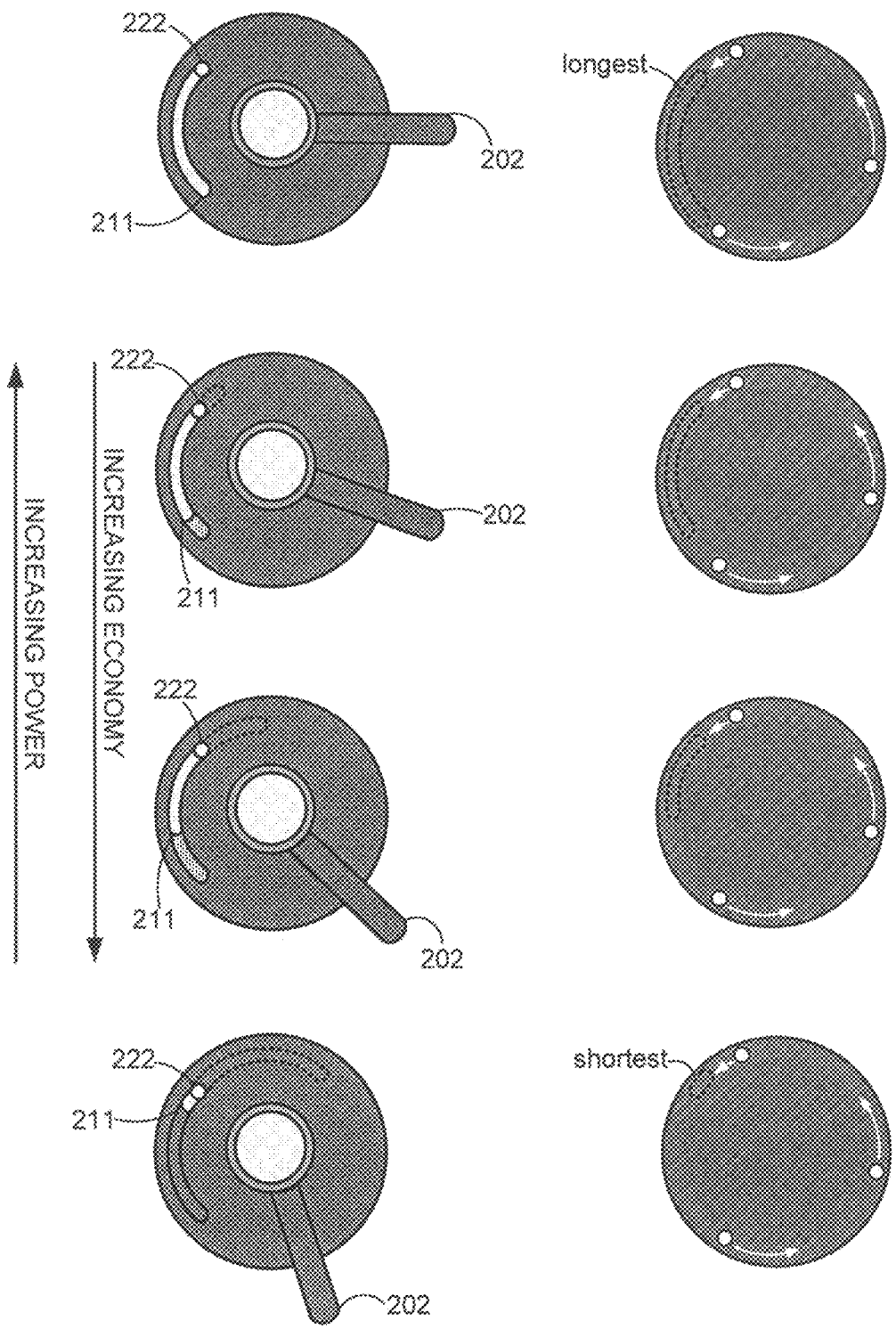

FIG. 15 diagrammatically depicts four different stroke settings of the duration valve of FIG. 13.

FIGS. 16-19 depict cutaway portions of the duration valve of FIG. 13 at the same stroke setting.

FIGS. 20-23 depict cutaway portions of the duration valve of FIG. 13 at a different stroke setting than FIGS. 16-19.

Figure 24:
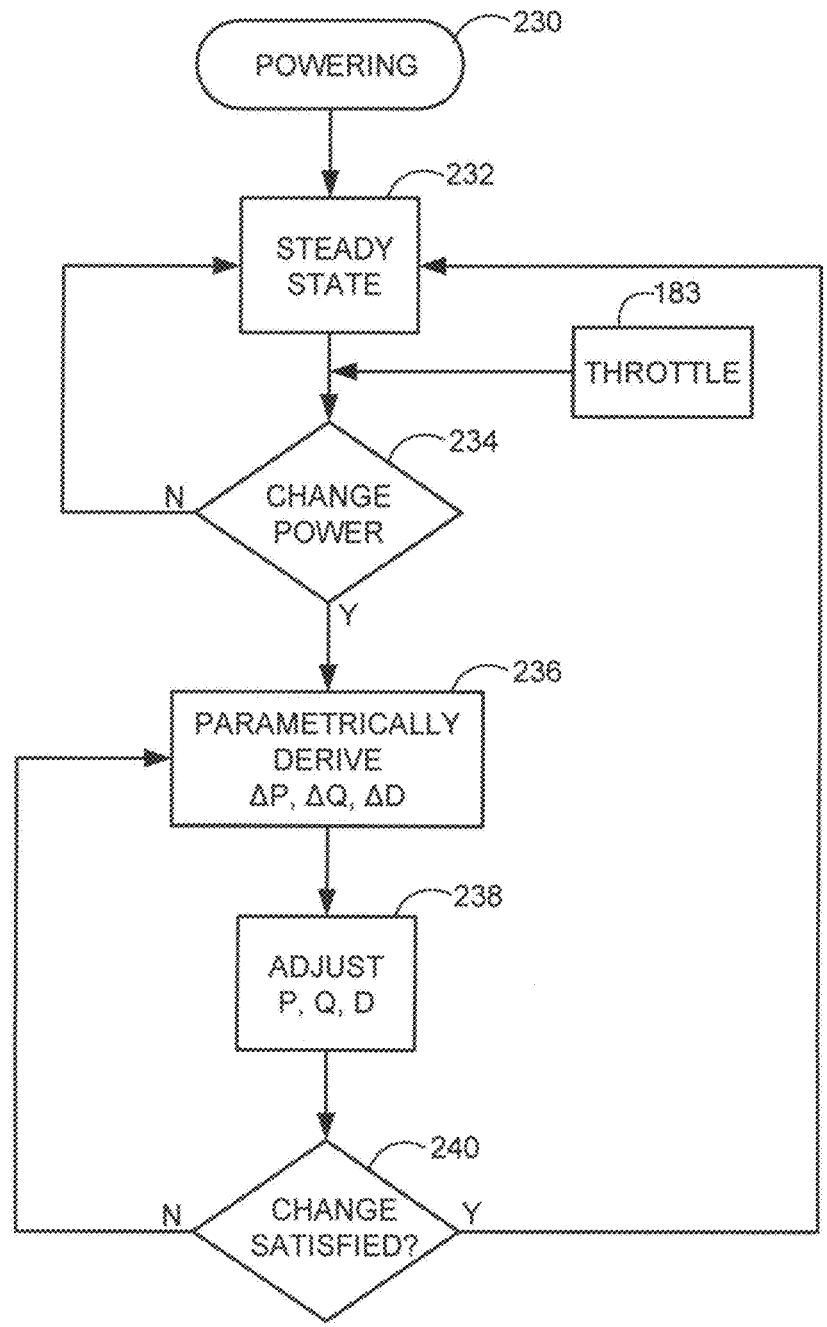

FIG. 24 is a flowchart depicting steps in a method for POWERING steam engines in accordance with embodiments of the present embodiments.

DETAILED DESCRIPTION

Generally, the embodiments of the present invention contemplate a rotary steam engine and associated methods of operation and control. Again, for clarity, for purposes of this description and the claimed embodiments the term "rotary" means generally that an expansion chamber for inlet steam is provided between a rotational rotor and a bore in the engine block, as opposed to in a reciprocating piston in a cylinder bore.

Figure 1:
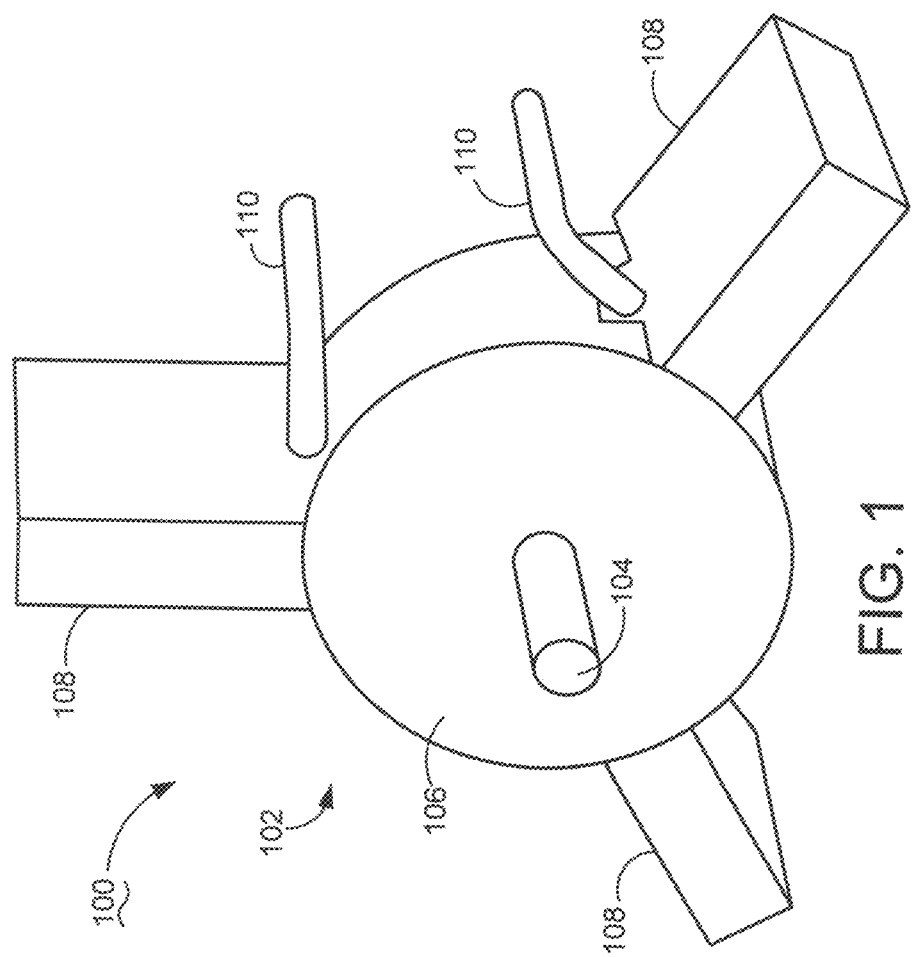
FIG. 1 is an isometric depiction of a single core and three lobe rotary steam engine constructed in accordance with embodiments of the present invention.

Particularly, FIG. 1 is an isometric depiction of a single core engine 100 that is constructed in accordance with embodiments of the present invention. The engine 100 has a hermetically sealed housing 102 having an internal surface (shown below) defining a bore forming an internal cavity where pressurized steam enters to act upon a rotor (shown below) which, in turn, imparts a rotational force to an output shaft 104. Most likely the housing 102 is stationary, such as by being attached to a frame (not shown), and the shaft 104 is connected to an external device, such as a gear (not shown) and rotated as a result of operating the engine 100 as designed in order to perform useful work with the external device. That premise is invoked for the purposes of this description, although the contemplated embodiments are not necessarily so limited. In alternative equivalent embodiments the shaft 104 could be stationarily affixed such as to a frame and the motor 100 operated to selectively position the housing 102 at desired rotational orientations.

The housing 102 has a central (in these illustrative embodiments circular) portion 106 and a plurality, in these illustrative embodiments three, protuberant portions 108 depending outwardly from the central portion 106. As described particularly below, the protuberant portions are housings in which vanes are reciprocatingly supported in a biased contacting engagement against a rotating rotor. The number of vanes matches the number of lobes on the rotor, such that the illustrative embodiments of FIG. 1 depict a three lobe design.

Exhaust lines 110 fluidly communicate low pressure steam from the internal cavity and preferably return the low pressure steam to a steam generator (depicted below) to be processed into high pressure steam again in a closed fluid system. Lubrication lines (not depicted) can be used in some embodiments to deliver a lubricant to the components in the internal cavity. In alternative equivalent embodiments, some or all of the internal components are coated with a suitable friction reducing material, such as aluminum magnesium boride (or "BAM"), eliminating any need for the externally supplied lubricant.

Importantly, details of particular construction such as the circular central portion 106, the radially straight protuberant portions 108, the three lobe design, and the arrangement of steam inlets and outlets, are merely illustrative of some embodiments of the present invention and as such are in no way limiting of all claimed embodiments. Equivalent alternative embodiments contemplate other arrangements, such as a non-circular central section and a different number and/or shape of the protuberant portions, for example, within a full contemplation of the embodiments of this invention.

Figure 2:
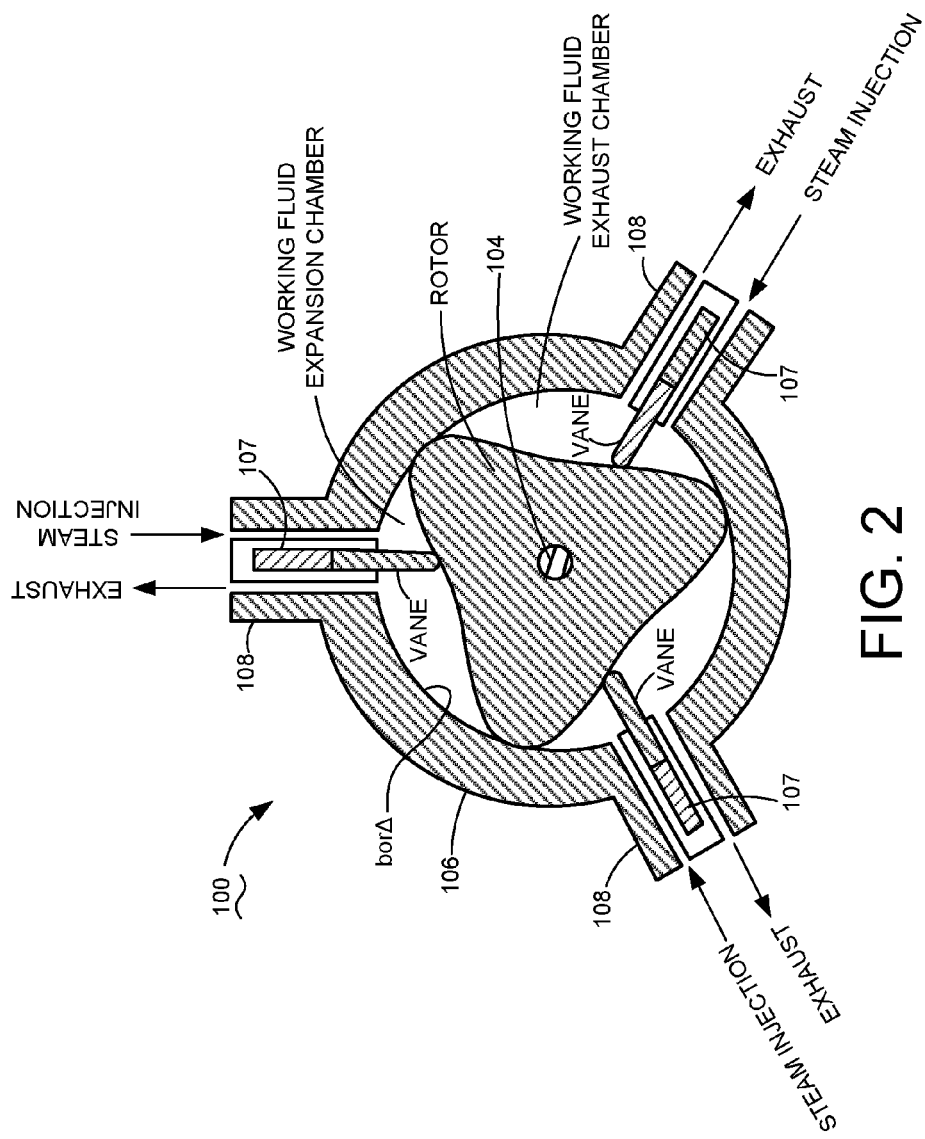
FIG. 2 is a cross-sectional depiction of the engine of FIG. 1.

FIG. 2 is a cross-sectional depiction of the three-lobe rotor engine 100 of FIG. 1. Three vanes are reciprocatingly supported in the housing 106, 108 and biased outwardly to maintain a sealing engagement against the perimeter surface of the rotor as it rotates, in these illustrative embodiments clockwise. For example, without limitation, compression members 107 such as but not limited to compression springs operably urge the distal ends of the vanes into the cavity to a pressingly sealing engagement against the rotating rotor.

Figure 3:
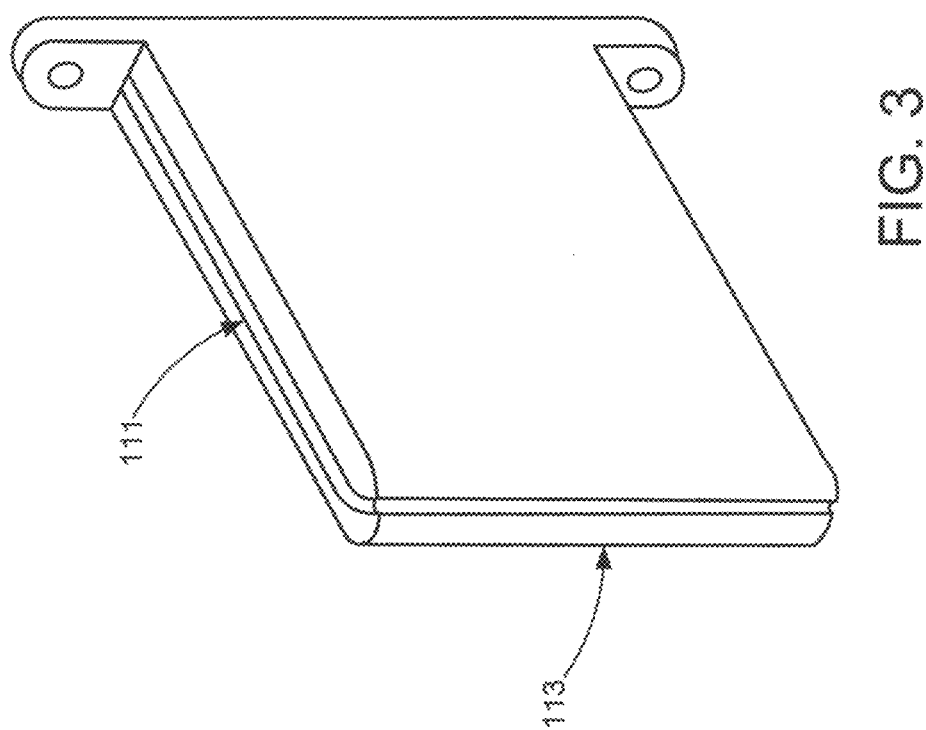
FIG. 3 is an isometric depiction of one of the straight vanes in the engine of FIGS. 1 and 4.

The vanes and the distal ends of the rotor lobes where they sealingly move along the bore divide the internal cavity into three volumetrically same-size working fluid expansion chambers where high energy steam is injected to expand and rotate the rotor, and into three volumetrically same-size working fluid exhaust chambers where comparatively low energy (previously expanded) steam is exhausted back to the external combustion system, preferably in a closed loop external combustion cycle. As mentioned above, in some embodiments a lubricant may be injected from time to time to aid in reducing the frictional engagements of the moving parts. FIG. 3 is an isometric depiction of one of the vanes in FIG. 2, although the same can be said for the arcuate vanes described below. The vane can be provided with a channel 111 extending longitudinally along the vane and open at a distal end 113 thereof. A lubricant supply line (not depicted) can terminate in the protuberant portion 108 to fluidly communicate a predetermined measure of lubricant to the channel 111. A wiper (not depicted) that is likewise supported by the protuberant portion 108 can sealingly engage the channel 111 above where the lubricant is injected, and there continuously seal against the channel 111 as the vane reciprocatingly engages the rotor to prevent blowback of the lubricant and force the lubricant onto the rotor.

Figure 4:
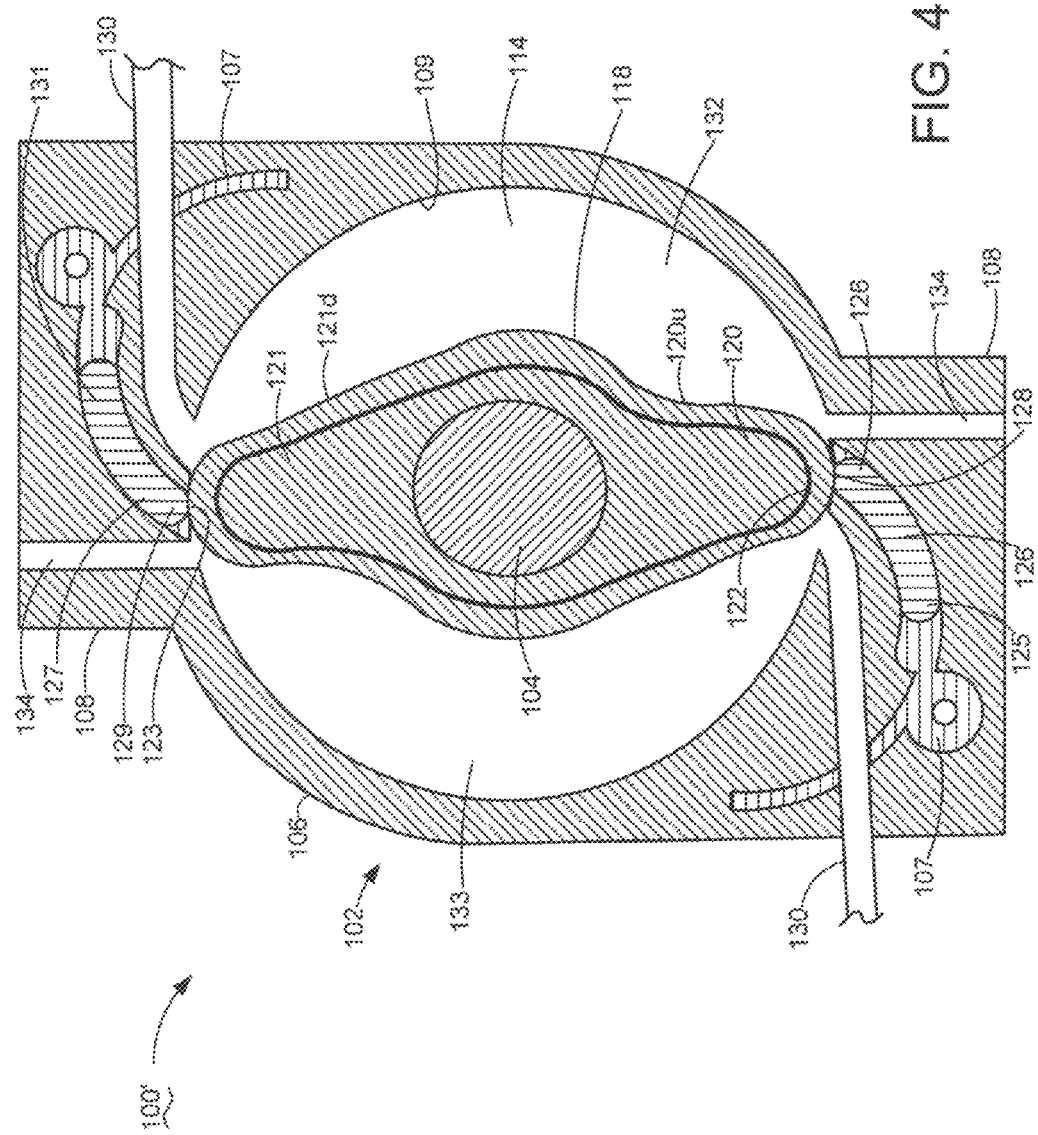
FIG. 4 is a cross-sectional depiction similar to FIG. 2 but of a two lobe rotary steam engine constructed in accordance with embodiments of the present invention.
Figure 5:
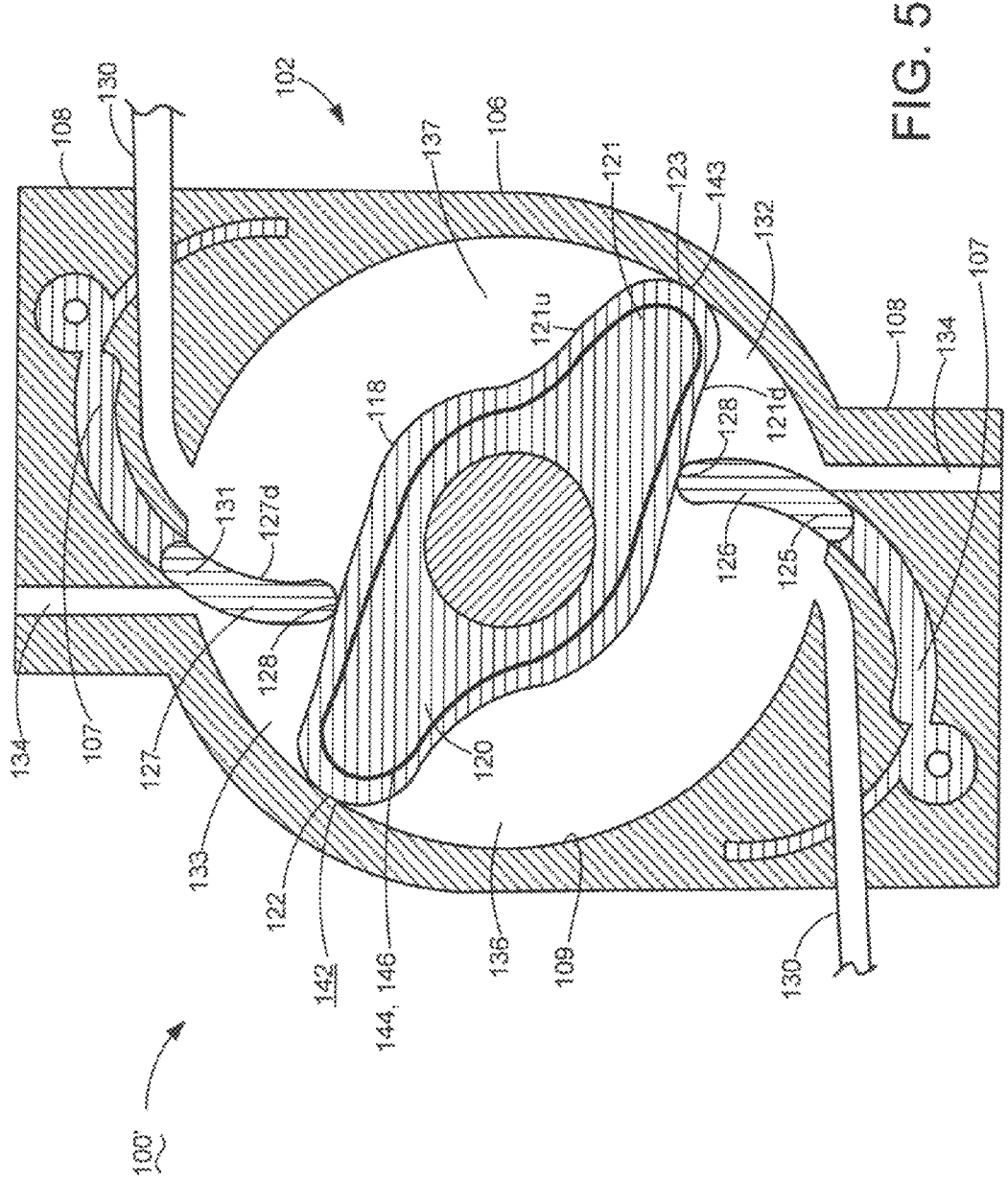
FIG. 5 is a cross-sectional depiction similar to FIG. 4 but showing the rotor in a different rotational position.

Turning now to FIGS. 4 and 5 which are cross section diagrammatical depictions of a steam engine 100' similar to that depicted in FIGS. 1 and 2 but for depicting equivalent alternative embodiments having only two protuberant portions 108, and hence of a two lobe design rather than the three lobe design of FIG. 1. The two lobe design advantageously provides for an optimal expansion chamber and exhaust chamber arrangement for a comparatively small size engine, such as would be well suited for use in powering a motor vehicle. Comparatively larger engines, meaning those of a comparatively larger diameter cavity, are optimized with a design incorporating more than two lobes in proportion to size.

The central portion 106 of the housing 102 has a bore 109 defining a central cavity 114. A rotor 118 in these illustrative embodiments has two opposing protuberant lobes 120, 121. Each lobe has a distal end 122, 123, respectively, that moves arcuately along the bore 109 as the rotor 118 rotates. FIGS. 4 and 5 depict different rotational positions of the rotor 118 within the cavity 114. In the description that follows the rotor 118 position in FIG. 4 is referred to as the neutral rotor position, and the rotor 118 position in FIG. 5 is referred to as one of the power stroke rotor positions.

A like plurality (same number as there are lobes) of vanes 126, 127 are reciprocatingly supported in the protuberant portions 108. In these illustrative embodiments the vanes 126, 127 are arcuate to reduce the height of the engine 100' across the distal ends of the protuberant portions 108. However, the contemplated embodiments are not so limited in that in equivalent alternative embodiments the vanes 126, 127 can be straight or arcuate of another curvature, although not depicted. In any event, the vanes 126, 127 are biased outwardly by the compression members 107, such as but limited to a torsional spring driven gear engaging a gear extension of the vane 108, so that distal ends thereof 128, 129 operably engage a perimeter of the rotatable rotor 118, while respective medial portions 125, 131 of the vanes 126, 127 reciprocate through the bore 109 as the distance from the bore 109 to the rotating rotor 118 varies.

In the rotor neutral position depicted in FIG. 4 all of the lobes 120, 121 are simultaneously rotationally aligned with the vanes 126, 127. By "rotationally aligned" it is meant that the distal ends of the lobes 122, 123 simultaneously sealingly engage the respective vanes 126, 127. As discussed in detail below, in some embodiments a seal member can be supported by one or both of the lobes 120, 121 and vanes 126, 127 to effect that sealing engagement therebetween at the neutral rotor position.

In the neutral rotor position depicted in FIG. 4 two comparatively large working fluid exhaust chambers 132, 133 are formed between opposing sides of the rotor 118 and the bore 109, each of the exhaust chambers 132, 133 being in fluid communication with a respective working fluid outlet 134 intersecting the bore 109. In other words, in the neutral rotor position of FIG. 4 the working fluid exhaust chamber 132 spans from a downstream surface 121d of one of the lobes 121 to the upstream surface 120u of the other lobe 120. The terms "upstream" and "downstream" for purposes of this description are in reference to the direction of rotor 118 rotation, which is clockwise in these illustrative embodiments.

FIG. 5 depicts a subsequent time when the rotor 118 has rotated clockwise to a power stroke rotor position where high energy steam injected into respective working fluid expansion chambers 136, 137 expands to impart equivalent and complimentary torques (or rotational forces) on the rotor 118. It will be noted that the rotation from the neutral rotor position in FIG. 4 to the one of the power stroke rotor positions in FIG. 5 incrementally increases in size a like plurality of volumetrically equivalent working fluid expansion chambers 136, 137 that are each in fluid communication with a respective fluid inlet 130 intersecting the bore 109. The working fluid expansion chamber 137 is defined between the downstream surface 127d of the vane 127 and the upstream surface 121u of the lobe 121 of the rotor 118. Thus, the working fluid expansion chamber 137 is cross-sectionally defined as the area from between where the downstream surface 127d and the upstream surface 121u intersect the bore 109 and entirely along the bore 109 therebetween, to the dynamic intersection of the downstream surface 127d and/or the distal end 129 of the vane 127 against the perimeter surface of the rotor 118 as it rotates. The other working fluid expansion chamber 136 is defined in like manner.

By "like plurality" (see above: "a like plurality of volumetrically equivalent working fluid expansion chambers . . . ") it is meant that the number of working fluid expansion chambers 136, 137 is the same as the number of lobes 120, 121 and corresponding vanes 126, 127. By "volumetrically equivalent" it is meant that that the working fluid expansion chambers 136, 137 are nominally the same size volumetrically in comparison to each other. In these illustrative embodiments of FIG. 5, for example, the two working fluid expansion chambers 136, 137 are at all times instantaneously the same size volumetrically; while incrementally increasing in size by rotation of the rotor 118, the working fluid expansion chambers 136, 137 remain the same size volumetrically with respect to each other. In this manner the same amount of steam energy injected simultaneously into each of the working fluid expansion fluid chambers 136, 137 (via the respective working fluid inlets 130) imparts an equivalent rotational force against the rotor 118.

It will be noted that the comparatively high energy steam is initially injected into and then expands in the working fluid expansion chambers 136, 137 to impart the rotational force against the rotor 118. The corresponding working fluid exhaust chambers contain comparatively low energy steam that is spent after having previously been expanded to rotate the rotor 118. Importantly, the spent steam in the working fluid exhaust chambers is advantageously exhausted without permitting premature condensation to occur to prevent water hammering either in the engine or in the external combustion system. As importantly, however, is the advantageous arrangement of the rotor 118 perimeter surface and the reciprocating shape of the vanes 126, 127 biased in constant contact against that surface to continually provide an existence of the working fluid exhaust chambers 132, 133 virtually throughout the entire range of the power stroke rotor positions. That reduces the backpressure acting against the high energy steam imparting the rotational force on the rotor 118 virtually throughout each power stroke. Particularly, for example, the power stroke rotor position depicted in FIG. 5 is one of a number in which the downstream surface 121d of the lobe 121 of the rotor 118 imparts a force that retracts the vane 126 toward the bore 109 downstream of the working fluid outlet 134 simultaneously as the distal end 123 of the lobe 121 moves arcuately along the bore 109 upstream of the working fluid outlet 134. The other volumetrically same-size working fluid exhaust chamber 133 continually vents the spent steam substantially throughout the entire power stroke of the other lobe 120 in the same manner.

An apex seal 142, 143 is supported at the distal end 122, 123 of each lobe 120, 121 that effects the necessary sealing engagement between each lobe 120, 121 and the bore 109 to segregate high energy steam in the working fluid expansion chamber 136, 137 on the upstream side of the respective lobe 120, 121 from low energy steam in the working fluid exhaust chamber 132, 133 on the downstream side of the respective lobe 120, 121. In these illustrative embodiments the apex seal 142, 143 can be partially recessed in and thereby extend as supported from a channel formed at the distal end 122, 123 of the lobes 120, 121. The contemplated embodiments are not so limited, however, in that in equivalent alternative embodiments the apex seal can be otherwise attached to the distal end 122, 123 such as by adhering thereto and the like, or the apex seal 142, 143 can be formed as a part of the distal end 122, 123, and the like. Opposing sides seals 144, 146 similarly sealingly engage the sides of the rotor 118 against central portions 106 of the housing 102.

Figure 6:
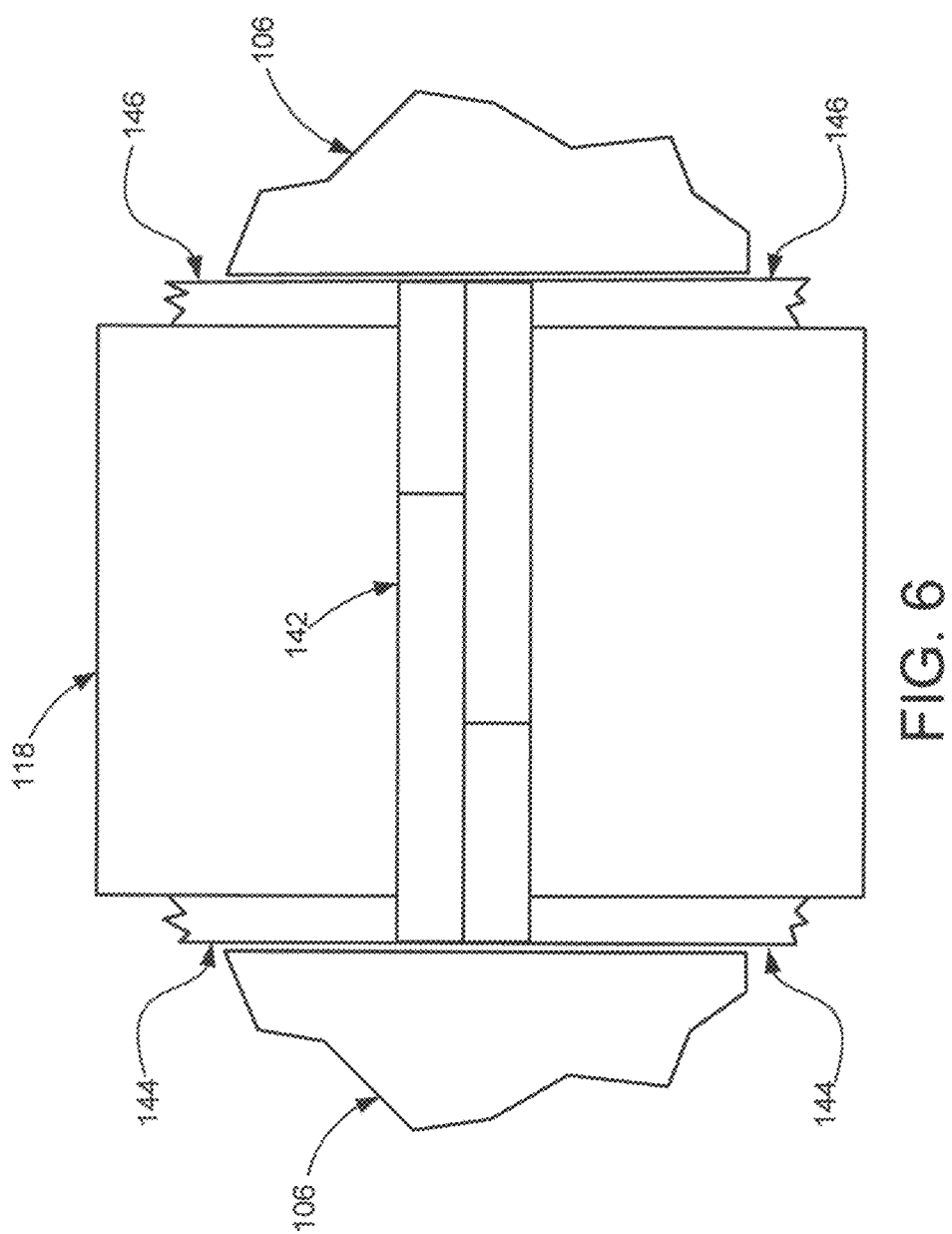
FIG. 6 is an end view depiction of the rotor lobe showing the apex and side seals on the rotor in FIGS. 4 and 5.
Figure 7:
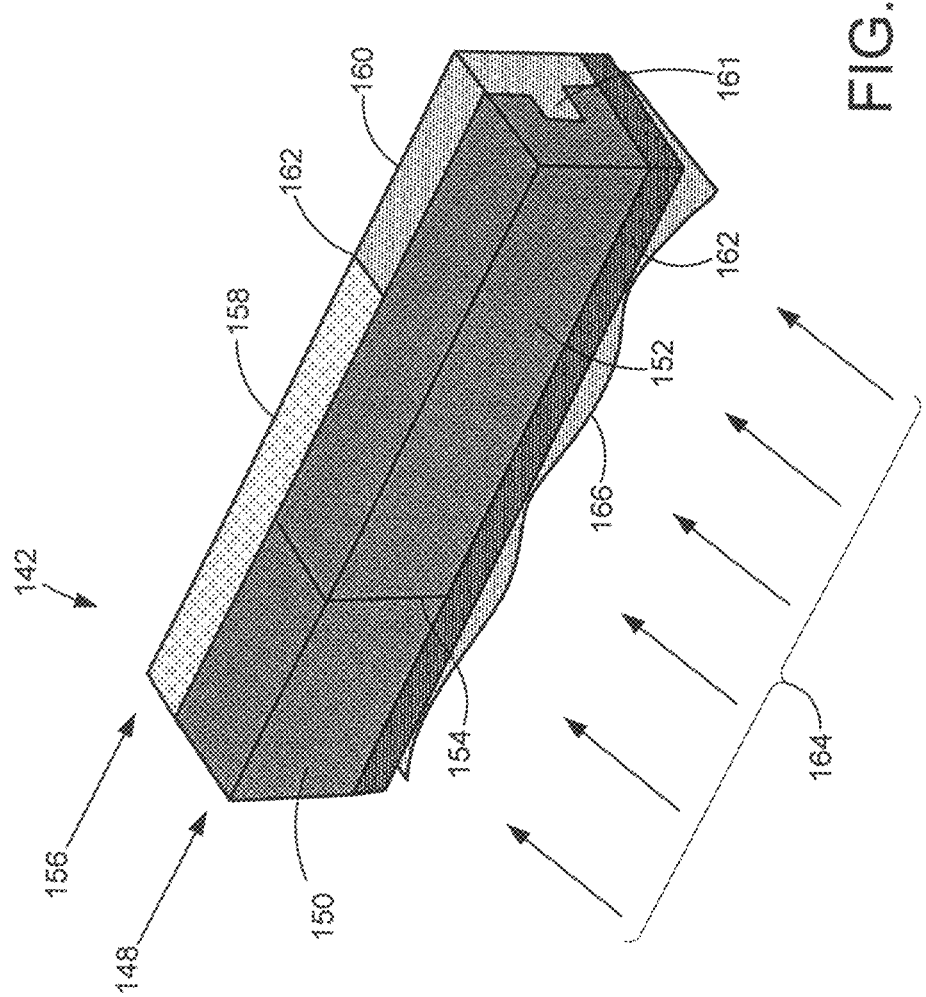
FIG. 7 is an enlarged isometric depiction of the apex seal removed from the distal end of the rotor.

FIG. 6 is an enlarged diagrammatic depiction of a distal end view of the rotor 118 as viewed by the bore 109 depicting the sealing engagement of the apex seal 142 against the bore 109 and the side seals 144, 146 against the opposing central portions 106 of the housing 102. FIG. 7 isometrically depicts the apex seal 142 removed from the supporting engagement of the lobe 118. In these illustrative embodiments the apex seal 142 has a first row 148 of seal segments 150, 152 defining a first seam 154 between adjacent seal segments 150, 152. Similarly, the apex seal 142 has a second row 156 of seal segments 158, 160 defining a second seam 162 between adjacent seal segments 158, 160. The seal segments 158, 160 have protuberant portions 161 that are receivingly engaged within cavities formed in the first row seal segments 150, 152 to radially interlock the rows of seal segments together. The seams 154, 162 are laterally staggered to ensure no direct fluid leakage pathway exists across both rows 148, 156 in the downstream direction as indicated by reference arrows 164.

In these illustrative embodiments a rigid base 162 affords a smooth sliding surface for each row 148, 156 of respective seal segments 150, 152 and 158, 160. An expansion member 166, such as the spring steel plate depicted, urges the rigid base 162 toward the distal end of the lobe 118 and, in turn, the rows 148, 156 of seal segments 150, 152 and 158, 160 against the bore 109.

Figure 8:
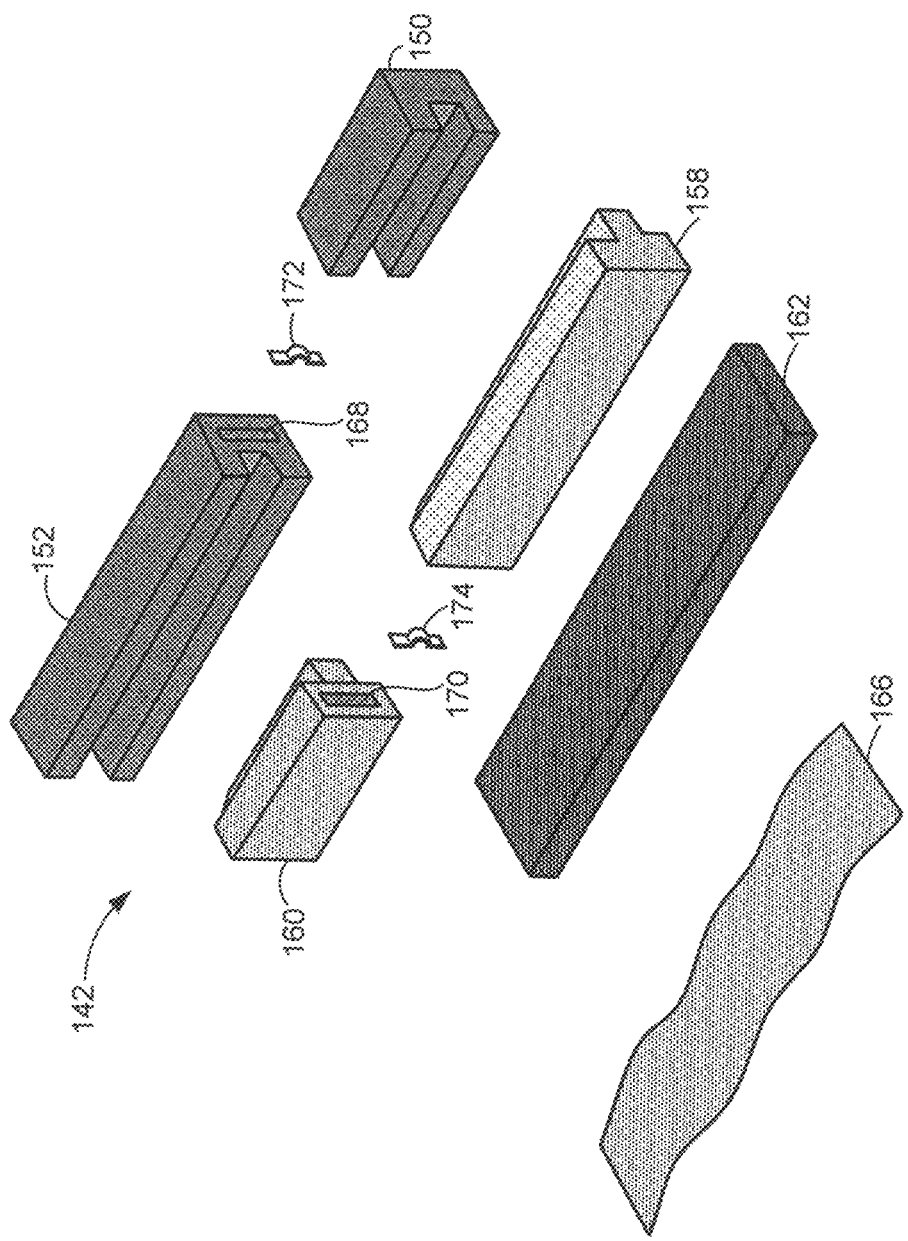
FIG. 8 is an exploded isometric depiction of the apex seal of FIG. 7.

FIG. 8 is an exploded isometric view from another perspective of the apex seal 142. Ends of the seal segments 152, 160 at the seams 154, 162 (FIG. 7) define cavities 168, 170 into which expansion members 172, 174 are seated and partially protrude therefrom to bias the mating seal segments 158, 160 and 150, 152 apart from each other at the staggered seams 154, 162 to otherwise make the sealing engagement of the opposing aligned edges of the apex seal 142 against the housing 102 more robust. The expansion member 172, 174 construction also creates a dynamic sealing interface that compensates for surface variations and for thermal variations during engine 100 operation. Distal edges of the seal segments 150, 152, 158, 160 can cooperatively define a radius edge in order to make a predefined contacting engagement, such as but not limited to a point-contacting engagement, with the bore 109.

The opposing side seals 144, 146 (FIG. 6) are of a similar construction to that described above, being provided between the opposing substantially planar sides of the rotor 118 and mating substantially planar surfaces of the central portion 106 of the housing 102.

Figure 9:
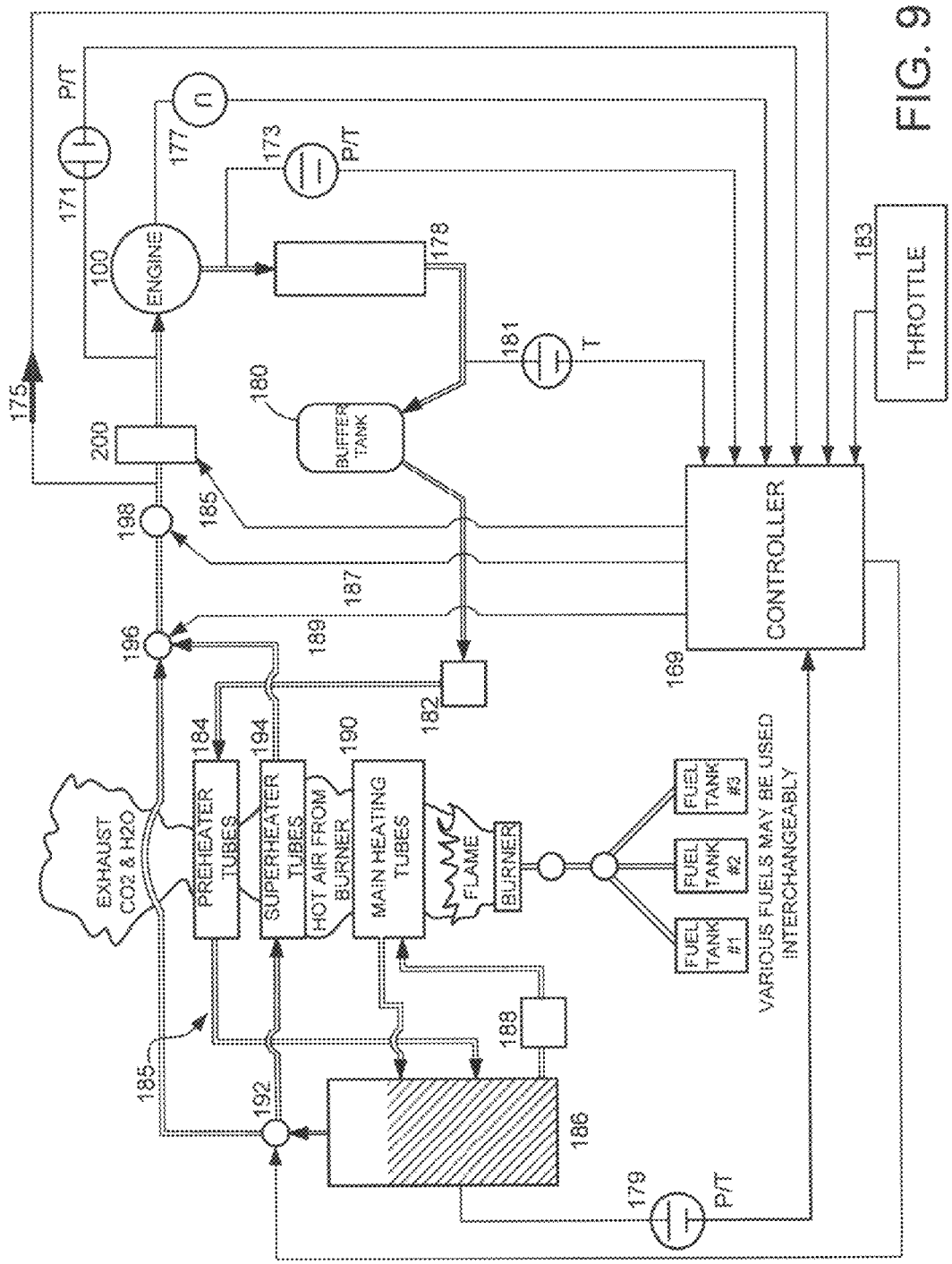
FIG. 9 is a functional block diagram of an external combustion system in accordance with illustrative embodiments of the present invention.

FIG. 9 is a functional block depiction of the engine 100 discussed heretofore along with an external combustion system suited for powering the engine 100 in accordance with illustrative embodiments of the present invention that are not in any way limiting of the contemplated embodiments of the present invention. The spent steam is output from the engine 100 from the working fluid exhaust chambers 132, 133 via the respective working fluid outlets 134 to a condenser 178. Condensate can be accumulated in a buffer tank 180 and routed via a pump 182 through preheater circuitry tubing 184 in a boiler 185 before being returned to a steam tank 186. Comparatively cooler condensate from the bottom of steam tank 186 is routed via recirculation pump 188 through main heating circuitry tubing 190 and returned to the steam tank 186 as the primary source of wet steam from the steam tank 186. A control valve 192 selectively diverts a portion of the wet steam from the steam tank 186 to superheater circuitry tubing 194. Again, importantly, these illustrative embodiments that depict the superheater source being energized by the same heat source that generates the steam in the steam tank 186 are not in any way limiting of the contemplated embodiments of the invention. That is, in alternative equivalent embodiments a separate heat source can be employed so that the superheated steam state can be thermally controlled entirely separately from that energy that is expended to generate the steam in the steam tank 186. Furthermore, in other equivalent alternative embodiments the superheated steam control can be accomplished without mixing wet stream and superheated steam, but rather by only additionally heating the steam generated by the steam tank 186.

In these illustrative embodiments, another control valve 196 selectively mixes the wet and superheated steam sources to deliver a desired state (or quality) of steam to a pressure valve 198. The pressure valve 198 selectively delivers the desired state of steam at a desired pressure to a duration valve 200. The duration valve 200 selectively delivers a desired pulse (interval of a selected duration) of steam at the desired quality and pressure to the working fluid inlets 130 of the engine 100.

A processor based control system includes a controller 169 that executes computer instructions that are stored in memory and that are executable to control the engine 100 throughout a wide range of operating conditions, from idle to maximum acceleration and all modes of operation therebetween. In the illustrative embodiments depicted here, not in any way limiting, the controller 169 receives thermodynamic state information such as steam pressure and steam temperature both upstream and downstream of the engine via sensors 171, 173, respectively. In these illustrative embodiments the sensors 171, 173 are depicted as being of a semiconductor construction although that is in no way limiting of the contemplated embodiments in that the skilled artisan readily ascertains other monitoring devices can be used equivalently such that no enumeration of all such types of devices is necessary to understand the scope of the disclosed subject matter of these embodiments.

A flow sensor 175 informs the controller 169 as to the amount of steam that is being delivered to the duration valve 200. A speed sensor, such as the tachometer 177 depicted, informs the controller of rotor 118 (FIG. 5) rotational speed. Another pressure/temperature switch 179 like those discussed above inform the controller 169 as to the pressure and temperature of the steam tank 186. A temperature sensor 181 informs the controller 169 as to the condensate temperature from the condenser 178. Finally, a throttle command 183 informs the controller 169 as to whether a change in power from present load conditions is being called for, such as a call for acceleration at a time when the engine 100 is producing a constant velocity steady state level of power.

Given the present operating state of the engine 100 and particularly in view of the observed engine speed (such as via tachometer 177) in comparison to the contemporaneous demand for power (such as via throttle command 183), the controller 169 parametrically optimizes power and efficiency by indexing stored power/efficiency curves that can be empirically tuned for the particular engine 100, such as by the setting of EEPROM registers at engine 100 break-in. The parametric optimization results in the controller 169 making adjustments to one or more of: (1) the amount of steam delivered to the engine 100 during each power stroke by modulating the duration valve 200 via communications link 185, and/or (2) the steam pressure by way of modulating the steam pressure valve 198 via communications link 187, and/or (3) the steam quality by way of modulating the mixing valve 196 via communications link 189.

Figure 10:
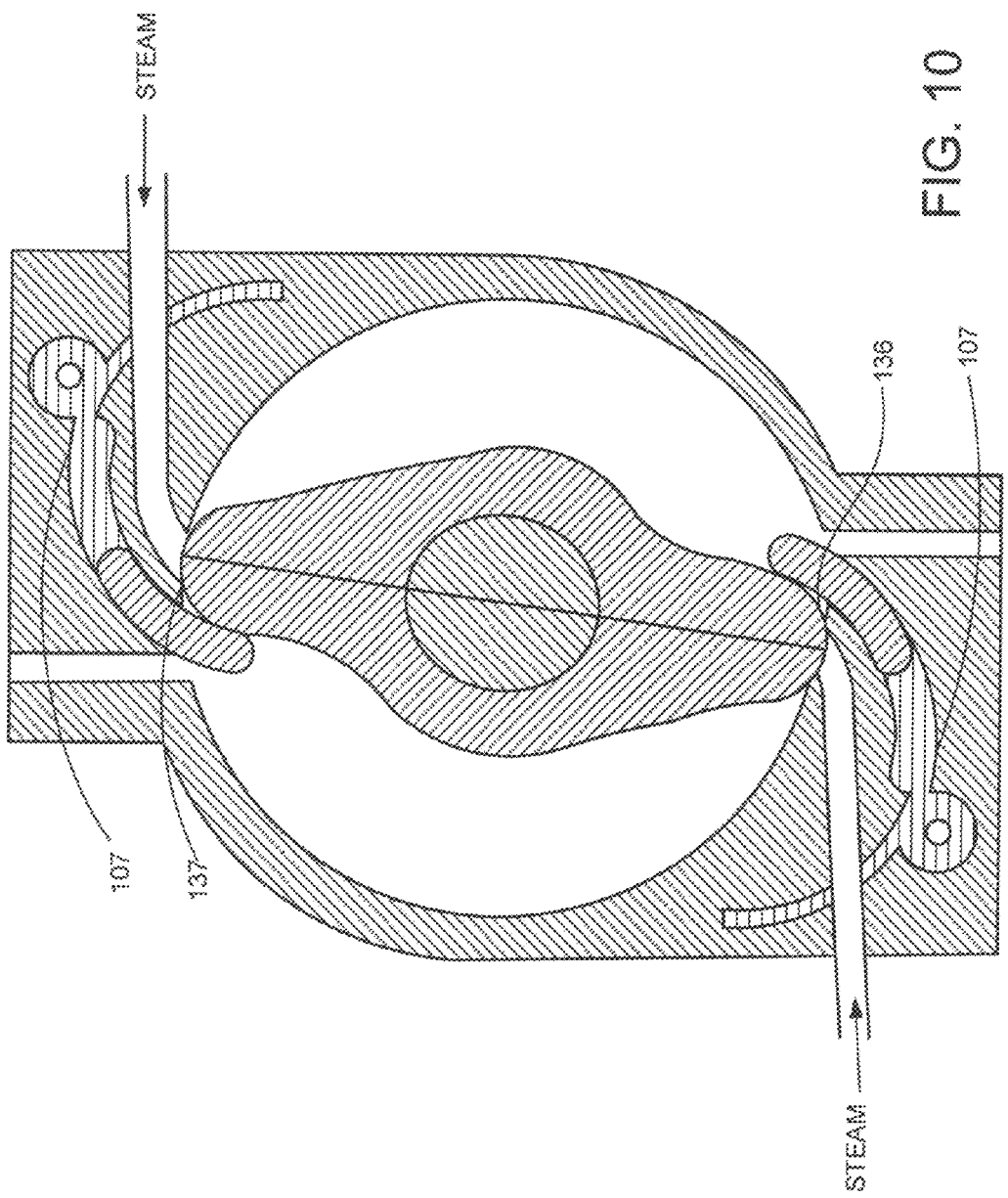
FIG. 10 is a cross-sectional depiction similar to FIG. 4 but showing the rotor in a different rotational position.
Figure 11:
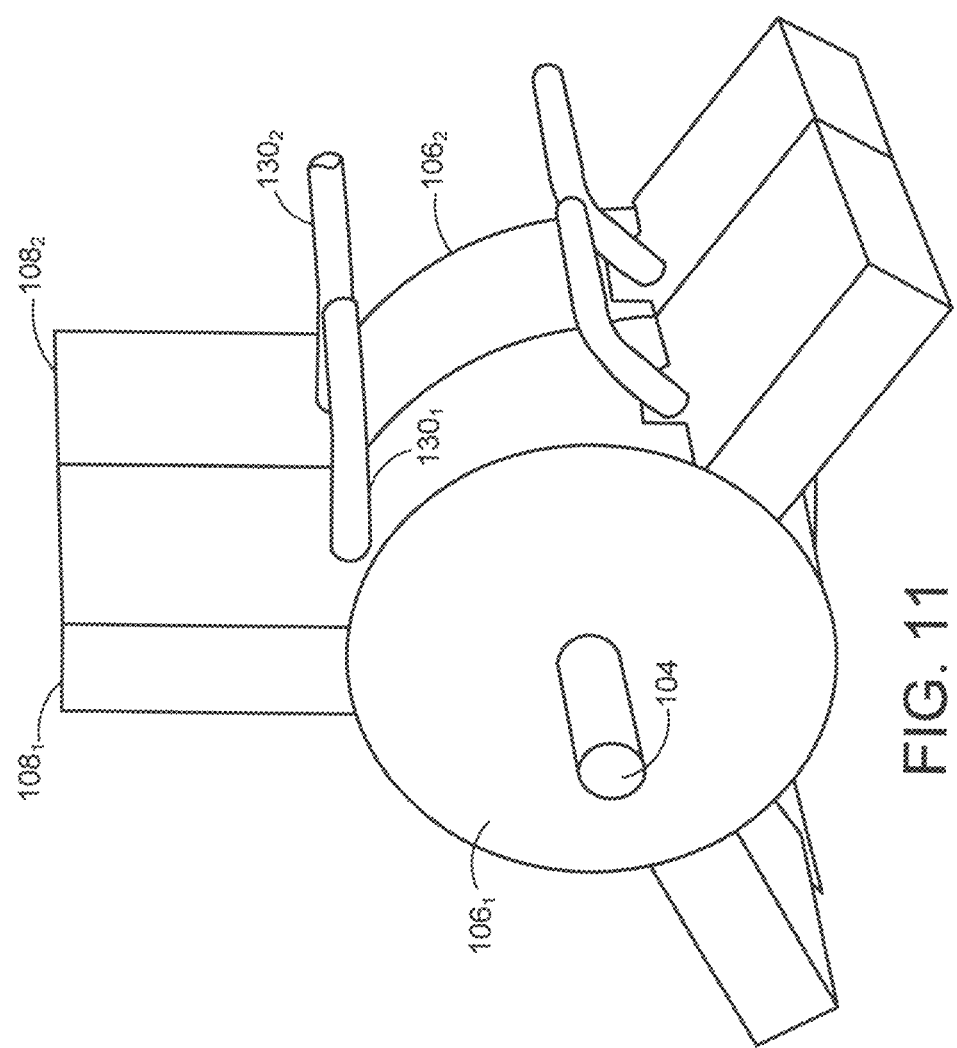
FIG. 11 is an isometric depiction similar to FIG. 1 but of a two-core engine constructed in accordance with embodiments of the present invention.

Returning momentarily to FIG. 4, at the neutral rotor position there depicted the duration valve 200 is not yet injecting the next burst of steam into the engine 100. Rather, the burst interval begins after a predetermined small rotation from the neutral position as depicted in FIG. 10. The additional rotation past the neutral rotor position where the next power stroke begins can be accomplished by the momentum previously imparted to the rotor 118 by the force keeping the rotor 118 in motion during the previous power strokes. Such would necessarily be the case where the engine 100 is constructed of only one rotor 118, as described so far and fully encompassed within the embodiments of the claimed invention. Such a construction is referred to herein as a "single-core" engine. However, in some alternative embodiments it can be advantageous to combine two or more rotors 118 with the same rotatable shaft. That is, FIG. 11 depicts a "two-core" version of the three lobe engine 100 depicted in FIG. 1, and FIG. 12 similarly depicts a "two-core" version of the two lobe engine 100' depicted in FIG. 4.

Figure 12:
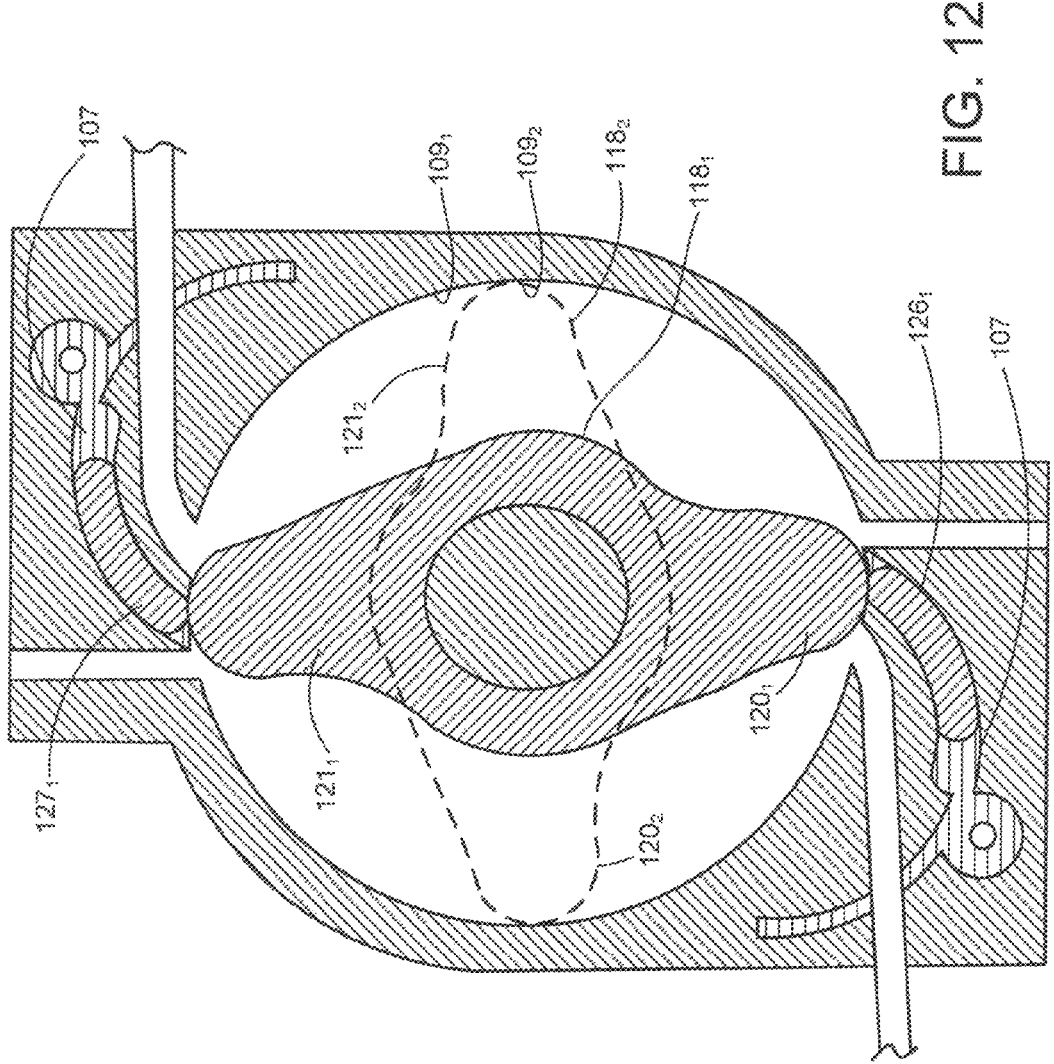
FIG. 12 is a cross-sectional depiction similar to FIG. 2 but of a two-core engine constructed in accordance with embodiments of the present invention.

Referencing FIG. 12 for example, the two-core engine has the first rotor $118_1$ rotating around the first bore $109_1$ and a second rotor $118_2$ rotating around a separately enclosed bore $109_2$. The first rotor $118_1$ is fixed in rotation with the shaft 104, having the two protuberant lobes $120_1$, $121_1$ that are alignable at the rotational position of the rotatable shaft 104 depicted in FIG. 12 with a like plurality of the vanes $126_1$, $127_1$. Note that the plurality of vanes $126_1$, $127_1$ in the first housing of these illustrative embodiments are rotationally aligned with the plurality of vanes $126_2$, $127_2$ in the second housing $102_2$. Thus, it will be clear that the second rotor $118_2$ is fixed in rotation with the same rotatable shaft 104 but has two protuberant lobes $120_2$, $121_2$, that are alignable at a different rotational position of the rotatable shaft than that depicted in FIG. 12 with a like plurality of the respective vanes $126_2$, $127_2$. The two-core engine of these illustrative embodiments also has a fluid handling arrangement that independently drives the first rotor $118_1$ and the second rotor $118_2$ via the working fluid. In some illustrative embodiments that can mean the external combustion system depicted in FIG. 9 and the descriptions thereof can advantageously include separately controllable control valves 192, 196, separately controllable pressure valves 198, and separately controllable duration valves 200 in relation to each of the two engine cores. In less complex designs the external combustion system would require at a minimum separately controllable duration valves 200 for each engine core because the timings of the steam bursts are different. Because of that difference, as best seen in FIG. 12, the previously injected burst of steam in the working fluid expansion chamber rotating the rotor $118_2$ would aid in rotating the rotor $118_1$ past the rotor neutral position in order to start the power stroke on that rotor $118_1$.

Having a plurality of staggered rotors $118_n$ in a multi-core engine also advantageously presents at least one of them in a position that is well suited for starting the engine from a cold start (rotor stopped). That is, at least one of the rotors $118_n$ will always be positioned such that an injection of high energy steam will expand with sufficient force against the respective rotor $118_n$ at its present rotational position in order to rotate it, beginning the entire engine in rotation. Alternatively, regardless of the number and staggered configuration selected, an auxiliary starter motor, such as an electric motor or a spring motor and the like, can be provided to rotate the rotor(s) 118 to a suited starting position. For purposes of this description, regardless of the specifics of the illustrative embodiments used for descriptive purposes, it will be understood that all structures and associated methods disclosed herein can equivalently be employed to individually power any desired number of rotors 118 within the same engine 100.

Returning now to FIG. 5 in view of the foregoing descriptions, it depicts the rotor 118 in one of the power stroke rotor positions after having rotated clockwise by the injection of the high energy steam into both of the working fluid expansion chambers 136, 137. The working fluid expansion chambers 136, 137 are sealed by the sealing engagement of the apex seals 142, 143 against the bore 109 and by similar lateral seals 144, 146 on the rotor 118, as previously discussed. The depicted illustrative embodiments depict the lateral seals 144, 146 substantially matching the contour of and inset substantially equidistantly from the vane 118 perimeter surface. That advantageously effectively provides a double seal between the working fluid expansion chamber 136, 137 opposing the working fluid exhaust chamber 132, 133 across each lobe 120, 121 of the rotor 118.

The high energy steam introduced into the working fluid expansion chambers 136, 137 there expands against the moveable lobes 120, 121 to impart a rotational force to rotate the rotor 118 and thus, in turn, to rotate the shaft 104. It will be noted that at this rotational position of the rotor 118 the working fluid expansion chambers 136, 137 are larger than the working fluid exhaust chambers 132, 133.

At some rotational position of the rotor 118, as is determined by a present demand for power from the engine, the injection of the high energy steam into the working fluid expansion chambers 136, 137 will be momentarily cut off. Even though the injection of steam ceases, the injected steam expands to continue rotating the rotor 118 through further power stroke rotor positions, until such time that the rotor 118 rotates far enough to establish a fluid communication between the working fluid expansion chamber and the working fluid outlet 134.

The optimum position for cutting off the injection of the high energy steam supply is calculable by a real time processor in relation to what amount of work potential there is in the expanding steam injected into the working fluid expansion chambers 136, 137. That is, it is calculable what work the injected steam, at a known inlet state and for a given duration, is capable of imparting to the rotor 118 for the incrementally increasing size of the working fluid expansion chambers 136, 137. The rotational position associated with size of working fluid expansion chambers 136, 137 that optimize the tradeoff between power and efficiency can be derived and controlled accordingly, with an adequate measure of safeguard against condensing noncompressible liquids in the fluid paths.

It has been determined that the optimal cutoff point for the steam injection varies from about ten degrees of rotation past the rotor neutral position to about eighty percent of the entire range of rotor power stroke positions, depending on the present demand for power from the engine in view of environmental conditions. The entire range of rotor power stroke positions depends on the number of lobes; that is, it is about 180 degrees for a two lobe rotor and about 120 degrees for a three lobe rotor. Generally, the entire range of rotor power stroke positions is 360/N, where N is the number of lobes.

Importantly, it is advantageous to contain the residual heat from the injected and expanded steam inside the cavity even after the expanded steam is exhausted and a new power stroke cycle began. Although not depicted, it will be understood that preferably the entire core, each exposed external surface thereof, is covered with a thermally insulative material to retain the energy of the steam temperature to boost the initial energy conditions for subsequent power strokes. One such material well suited for such an application is an aerogel-based insulating material such as the product marketed as Thermablok® by Thermablok Thermal and Acoustic Isolation Systems of Tampa, Fla. In alternative equivalent embodiments additives can be included in the material of which the engine core itself is manufactured to increase its thermal insulative capability.

FIG. 13 is a view similar to FIG. 1 of a single-core and three-lobe engine having a duration valve 200 attached to the rotatable shaft 104 in accordance with embodiments of the present invention. The duration valve 200 has an armature 202 that is connectable to a control linkage (not shown) to variably control the amount of high energy steam that is injected into the working fluid expansion chambers 136, 137 during each power stroke. That is, moving the linkage to place the armature 202 at one extent of its rotational travel minimizes the power produced by the engine 100, by minimizing the duration of the injection of steam for each power stroke, and therefore maximizes the efficiency of operation. Conversely, moving the linkage to place the armature 202 at the opposite extent of its rotational travel maximizes the power produced by the engine 100, by maximizing the duration of the injection of steam for each power stroke, with a concomitant reduction in operating efficiency.

The duration valve 200 in these illustrative embodiments has an input plate 204 defining an input aperture 206 in communication with the supply of high energy steam from the steam generator (FIG. 9). The input aperture 206 fluidly communicates with an arcuate channel 208 formed in the interior surface of the input plate 204.

Figure 14:
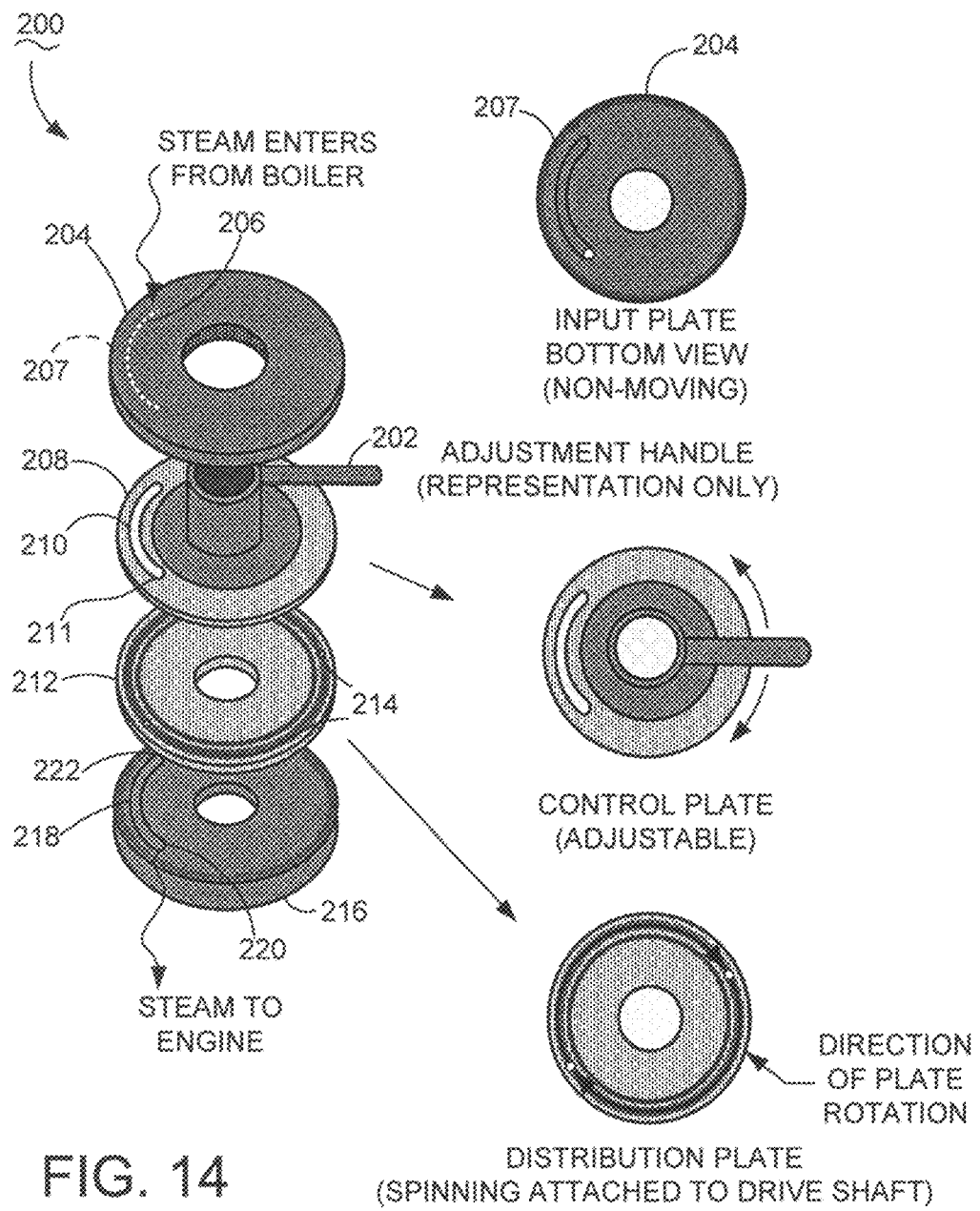
FIG. 14 is an exploded isometric depiction of the duration valve of FIG. 13 in accordance with embodiments of the present invention.

FIG. 14 is an exploded isometric depiction of the duration valve 200. A control plate 208 is selectively slidable in relation to the input plate 204, by selected actuation of the armature 202 which is connected to or formed as a portion of the control plate 208. The control plate 208 defines an arcuate slot 210 that is operably alignable to fluidly communicate with the channel 207 in the input plate 204. The slot 210 has an end 211.

A distribution plate 212 is likewise rotatable in relation to the input plate 204, and is affixed in rotation with the shaft 104 (FIG. 1). The distribution plate 212 defines a plurality of apertures 214, such as but not limited to the three aperture pattern depicted, which are radially disposed so as to selectively align at times in fluid communication with the slot 210 in the control plate 208.

An exit plate 216 like the input plate 204 is stationary, the two forming opposing portions of a sealed enclosure for operation of the control plate 208 and distribution plate 212. The exit plate 216 similarly has an arcuate channel 218 in fluid communication with a through aperture 220. An end 222 of the channel 218 is opposite the aperture 220. The high energy supply steam passing through the aperture 220 is directed to the working fluid inlets 130 in the engine and thereby destined for the respective working fluid power chambers 136, 137.

The continuous rotation of the distribution plate 212 in cooperation with the selected setting of the control plate 208 forms a variably sized flow path through which the steam must first traverse before being injected into the engine. FIG. 15 depicts four different settings of the armature that define the longest and shortest strokes, or steam flow paths through the duration valve 200, between one end of the slot 222 and an opposing end of the slot 211 in the top and bottom views, respectively. That is, the comparatively longest stroke in the top view admits a longer duration of steam injection than the comparatively shortest stroke in the bottom view.

Figure 16:
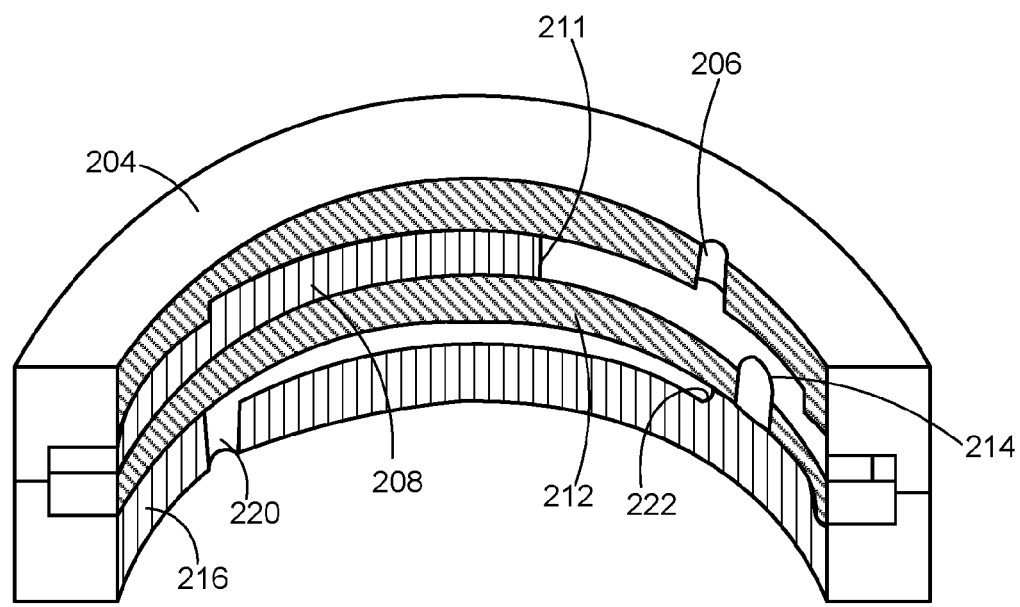

FIG. 16-19 diagrammatically depict cutaway portions of the duration valve 200 for a comparatively lower stroke setting of the control plate 208 FIG. 16 depicts a time when the rotational position of the distribution plate 212 is such that the supply of high energy steam to the engine 100 is momentarily cut off. Note that in this rotational position of the distribution plate 212 its aperture 214 has not yet rotated into fluid communication with the channel 218 in the exit plate 216. Therefore, the high energy supply of steam is communicated to the slot 210 that is sandwiched between the input plate 204 and the distribution plate 212, and is likewise communicated to the aperture 214 in the distribution plate 212 because it has rotated into fluid communication with the slot 210 in the control plate 208. However, because the aperture 214 in the distribution plate 212 has not yet rotated into fluid communication with the channel 218 in the exit plate 216, the supply of high energy steam to the engine 100 is deadheaded against the exit plate 216 and thereby momentarily cut off. Although not depicted, it will be understood that in previous instantaneous moments the aperture 214 in the distribution plate can be at a position where it is not yet in fluid communication with the slot 210 in the control plate 208. In that case, the supply of high energy steam to the engine 100 will likewise be cut off but in that case deadheaded against the distribution plate 212.

The amount of high energy steam that is ultimately admitted into the engine 100 depends on how long, in other words the duration, the aperture 214 communicates fluid from the slot 210 in the control plate 208 to the channel 218 in the exit plate 216. That duration is particularly defined in terms of the arc length from the fixed position of the end 222 of the channel 218 in the exit plate 216 to the variably positionable end 211 of the slot 210 in the control plate 208.

Figure 17:
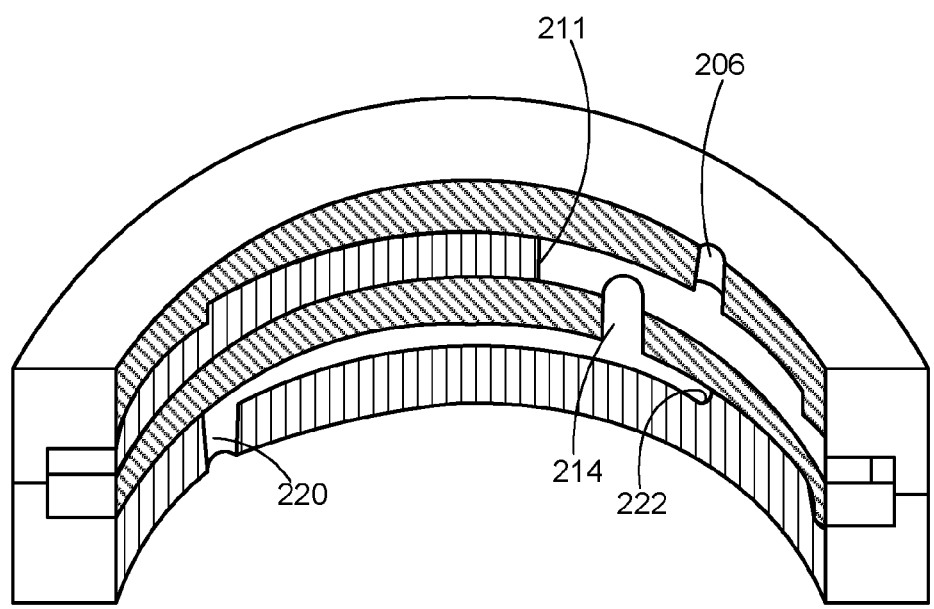
Figure 18:
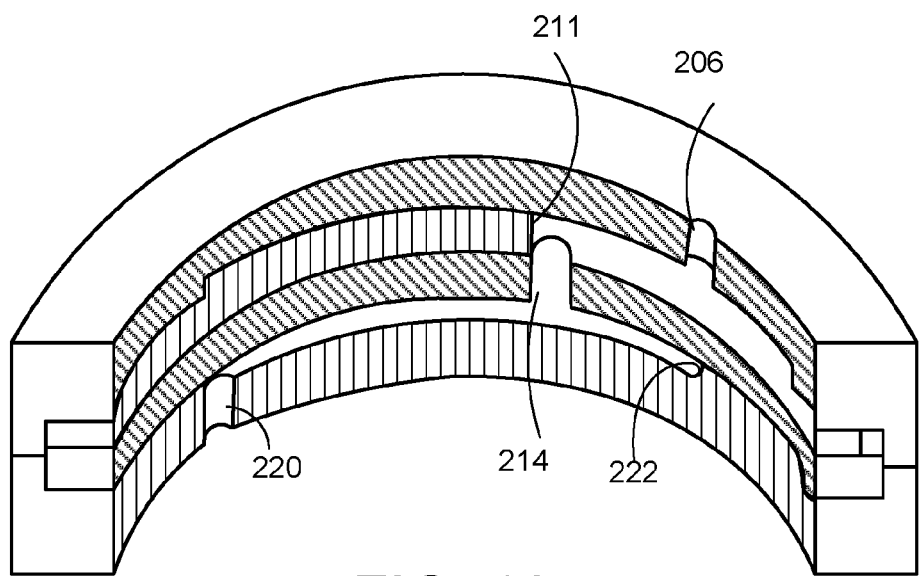
Figure 19:
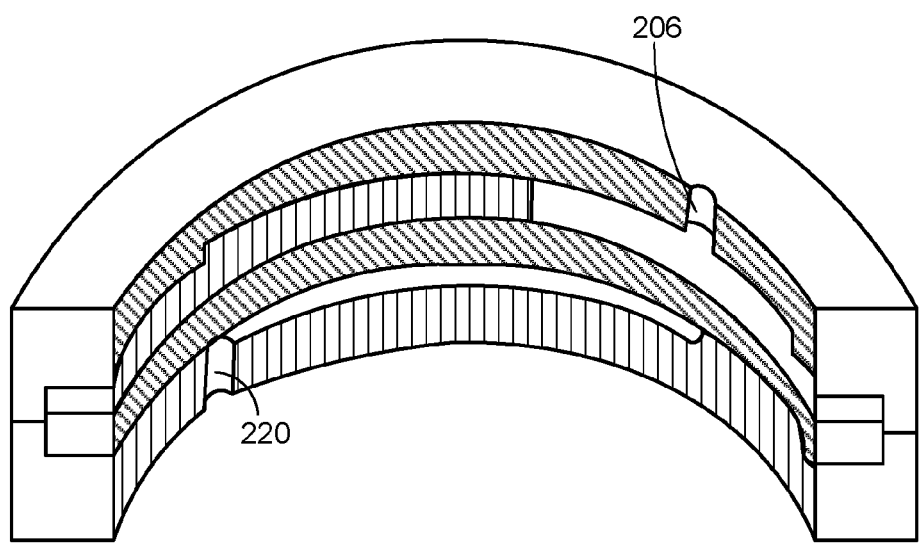
Figure 20:
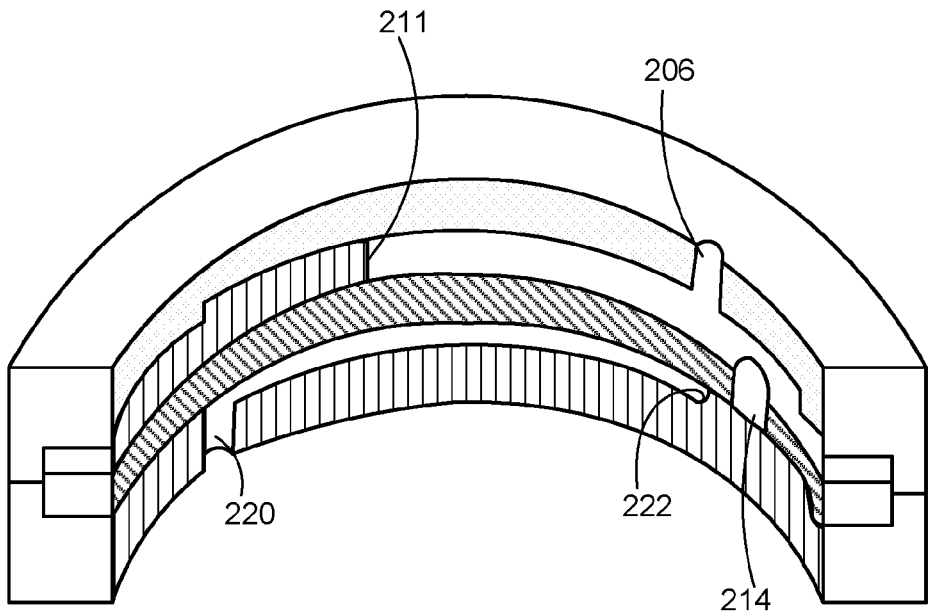

In FIG. 17, depicting the same power stroke setting of the control plate 208, the aperture 214 has at this time rotated far enough to establish a fluid communication with the channel 218 in the exit plate 216. Hence, as depicted by the arrow, a pathway is defined for the steam to flow through the duration valve and then into the inlets 130 of the engine 100. FIG. 18 depicts even further rotation of the aperture 214 but still in fluid communication with the channel 218 of the exit plate 216, such that the injection of steam into the engine 100 continues. FIG. 19 depicts the aperture 214 having rotated beyond the end 211 of the slot 210 in the control plate, ending the interval of steam injection into the engine as depicted by the arrow. FIGS. 20-23 are similar to FIGS. 16-19 except for depicting a different, comparatively longer power stroke setting of the control plate 208.

The duration valve 200 is fluidly coupled to the pressure valve 198 (FIG. 9) between it and the source of the steam, such as a steam boiler 185 as described above. The controller 169 executes computer instructions stored in memory to parametrically monitor the load profile demanded of the engine 100 in order to deliver an appropriate state of the supply steam that optimizes the balance between adequate power and optimal efficiency. For example, without limitation, an engine constructed in accordance with the present embodiments can be used to propel a vehicle. When the vehicle is initially moved from a complete stop the pressure valve can advantageously deliver a comparatively high pressure and/or high temperature state for the supply of steam in response to a call for a maximum power mode from the engine. Conversely, after the vehicle has been accelerated to and then operated at a substantially constant velocity, the pressure valve can respond to the observed parameters and advantageously reduce the pressure and/or the temperature and yet sustain a call for a reduced power mode that is capable of maintaining a cruising speed for the vehicle.

Figure 21:
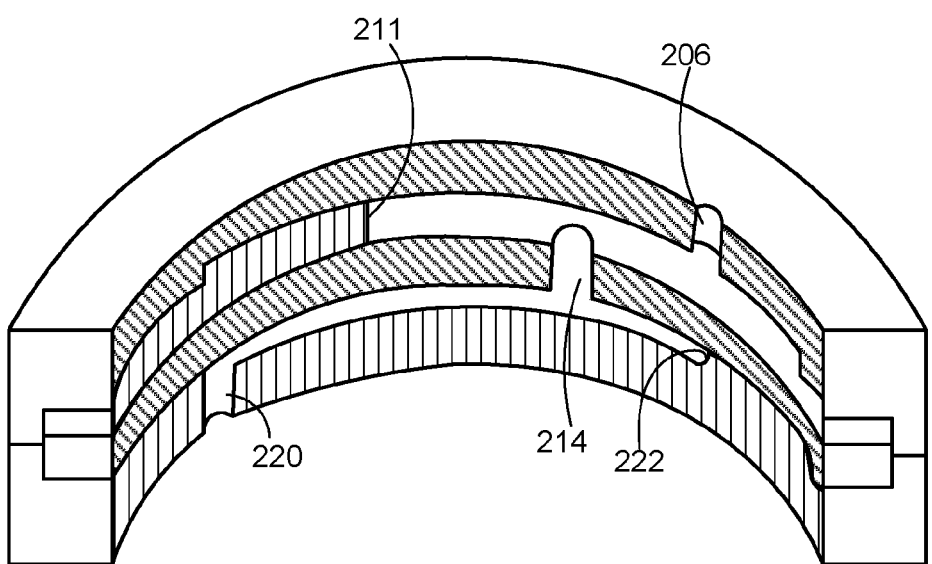
Figure 22:
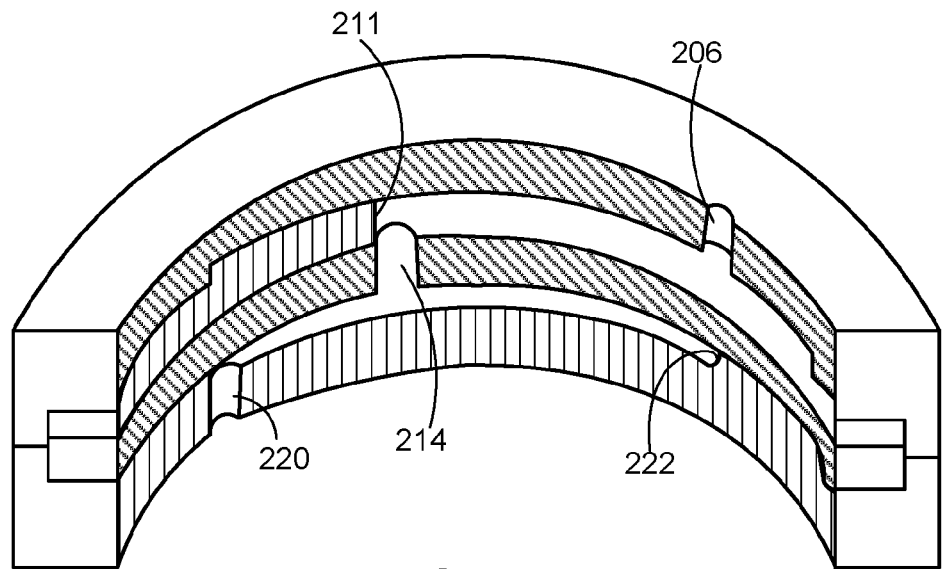
Figure 23:
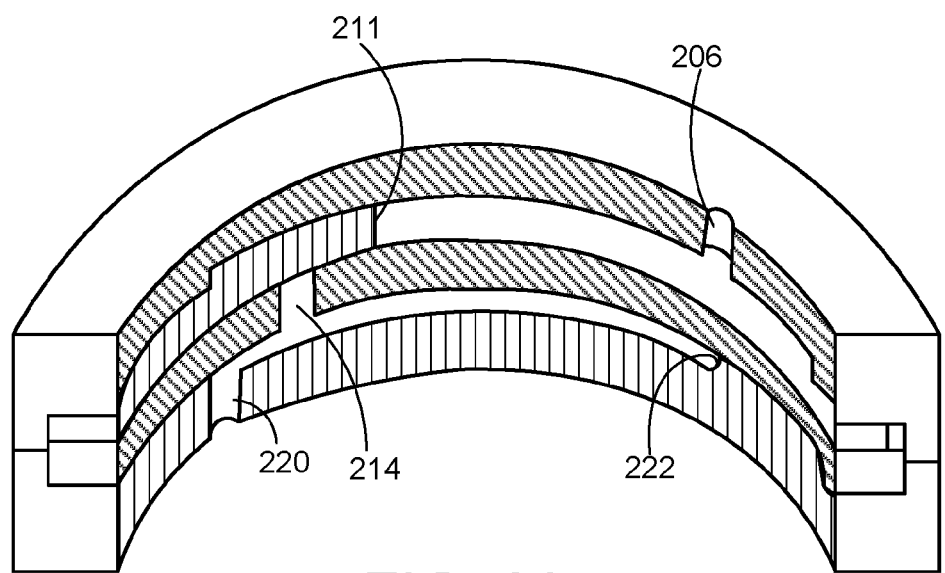

FIG. 21 is a flowchart of steps in a method 230 for POWERING the engine 100 in accordance with illustrative embodiments of the present invention. These embodiments of the method presume that a substantially steady state of operation is ultimately desired, as depicted in block 232, such as the constant velocity output of an engine constructed as described herein and mounted in a freight-hauling truck being driven over a long distance. In block 234 it is determined whether a change in power is being called for, such as might be the case where the truck begins ascending (more power demanded) or descending (less power demanded) a hill, or perhaps in response to the driver pressing the throttle 183 (FIG. 9) in order to otherwise accelerate the truck. If the determination of block 234 is "no," then control remains with the substantially steady state condition in block 232.

If, however, the determination of block 234 is "yes," then the controller (FIG. 9) parametrically derives the optimal adjustments from the current settings of one or more of the steam pressure, the steam quality, and/or the steam duration in block 236. Those one or more derived adjustments are implemented via the control system in block 238. In block 240 it is determined whether the demanded change in power has been satisfied by the adjustments made in block 238. If the determination of block 240 is "no," then control returns to block 236 and control adjustment continues iteratively. If the determination of block 240 is "yes," then control returns to the substantially steady state condition in block 232.

It is to be understood that even though numerous characteristics and advantages of various embodiments of the invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, features of the illustrated embodiments can be interchanged and the particular elements may vary depending on the particular application while maintaining substantially the same functionality without departing from the scope and spirit of the present invention. In addition, although preferred embodiments described herein are illustrated with respect to a system it will be appreciated by those skilled in the art that the teachings of the present invention can be applied to other systems without departing from the scope and spirit of the present invention.

What is claimed:

1. A rotary engine comprising:
    a housing having a bore defining a cavity;
    a rotatable rotor in the cavity having a plurality of protuberant lobes, each lobe having a distal end operably moving arcuately along the bore;
    a plurality of vanes, each vane having a distal end biased to operably engage a perimeter of the rotatable rotor, the distal end extending from a portion of the vane operably reciprocating through the bore; and
    a steam generator injecting steam into the bore to operably rotate the rotor between neutral rotor positions where all of the lobes are simultaneously rotationally aligned with the vanes, and a range of power stroke rotor positions between consecutive neutral rotor positions incrementally increasing in size a plurality of higher pressure steam expansion chambers each defined between the rotor and a respective rotationally upstream vane and each in fluid communication with a respective steam inlet intersecting the bore and simultaneously admitting steam into each, and incrementally decreasing in size a plurality of lower pressure steam exhaust chambers each defined between the rotor and a respective rotationally downstream vane and each in continuous fluid communication with a respective steam outlet intersecting the bore, all of the steam expansion chambers having equivalent volumes throughout the range of power stroke rotor positions and all of the steam exhaust chambers having equivalent volumes throughout the range of power stroke rotor positions, and at least some of the exhaust chambers characterized by the rotor perimeter surface retracting each vane toward the bore rotationally downstream of the respective steam outlet simultaneously as the distal end of the respective adjacent upstream lobe moves along the bore upstream of the same steam outlet; and
    a duration control controlling the steam injection to begin after the rotor has rotated past the neutral rotor position and for a selected continuous duration ending before the rotor rotates to the next rotor neutral position, the rotor rotation caused by expansion of the steam contained in each steam expansion chamber; and
    a steam controller selectively varying the amount of energy obtained from the steam that is simultaneously injected into each of the working fluid expansion chambers.

2. The rotary engine of claim 1 wherein each of the steam expansion chambers is bounded entirely by the bore between the intersection of the vane and the bore and the contacting engagement of the distal end of the lobe against the bore.

3. The rotary engine of claim 1 wherein the rotor neutral position is characterized by each steam exhaust chamber spanning from a downstream surface of one of the lobes to an upstream surface of the adjacent downstream lobe.

4. The rotary engine of claim 1 wherein the duration control ends the injection of the steam when the power stroke rotor position is more than about ten degrees past the previous neutral rotor position.

5. The rotary engine of claim 1 wherein the duration control ends the injection of the steam when the power stroke rotor position is less than about eighty percent of the entire range of rotor power stroke positions in degrees past the previous neutral rotor position.

6. The rotary engine of claim 1 wherein the rotor is fixed in rotation with a shaft, and the duration control is characterized by a duration valve comprising:
    a distribution plate fixed in rotation with the shaft and defining a first aperture;
    an input plate defining a second aperture joined to an output plate defining a third aperture forming an enclosure containing the distribution plate; and
    a control plate defining a fourth aperture and disposed in the enclosure between the distribution plate and one of the input plate and output plate, the control plate selectively positionable to vary the duration that the second aperture is in fluid communication with the third aperture via the first aperture as it operably moves in relation to the fourth aperture by the operable rotation of the shaft.

7. The rotary engine of claim 1 wherein each lobe has a seal at a distal end thereof in operable sealing engagement against the bore, the seal having a longitudinally extending first row of seal segments defining a first substantially orthogonal seam between adjacent seal segments, and the seal having a longitudinally extending second row of seal segments defining a second substantially orthogonal seam between adjacent seal segments, the first and second seams staggered laterally.

8. The rotary engine of claim 7 wherein one of the seal segments in the first row defines a protuberant portion, wherein one of the seal segments in the second row defines a cavity, and wherein the protuberant portion is sized to be receivingly engaged in the cavity to radially interlock the two rows.

9. The rotary engine of claim 7 comprising a first expansion member between the adjacent seal segments forming the first row, and a second expansion member between the adjacent seal segments forming the second row.

10. The rotary engine of claim 9 comprising a rigid base supporting both of the rows of seal segments and a third expansion member urging the rigid base toward the distal end of the lobe and, in turn, urging the seal segments in the sealing engagement against the bore.

11. The rotary engine of claim 1 wherein each vane reciprocating through the bore comprises opposing parallel arcuate upstream and downstream surfaces.

12. A rotary engine comprising: a first rotor fixed in rotation with a rotatable shaft, the first rotor having a plurality of protuberant first lobes that are alignable at a first rotational position of the rotatable shaft with a like plurality of first vanes each biased at a distal end against the first rotor during rotation;
   a second rotor fixed in rotation with the rotatable shaft, the second rotor having a plurality of protuberant second lobes that are alignable at a different second rotational position of the rotatable shaft with a like plurality of second vanes each biased at a distal end against the second rotor during rotation;
   a fluid handling arrangement that independently drives the first and second rotors via a working fluid; wherein
   the first rotor rotates within a first cavity defined by a first bore and the second rotor rotates within a second cavity defined by a second bore, the first and second vanes each operably reciprocating through the first and second bores, respectively, the first and second rotors operably rotating between neutral rotor positions where all the respective lobes are simultaneously rotationally aligned with the respective vanes, and a range of power stroke rotor positions incrementally increasing in size a working fluid expansion chamber defined between each rotor and a respective rotationally upstream vane in fluid communication with a respective working fluid inlet intersecting the respective bore, and incrementally decreasing in size a working fluid exhaust chamber defined between each rotor and a respective rotationally downstream vane each in continuous fluid communication with a respective working fluid outlet intersecting the respective bore, all of the steam expansion chambers having equivalent volumes throughout the range of power stroke rotor positions and all of the steam exhaust chambers having equivalent volumes throughout the range of power stroke rotor positions, and at least some of the power stroke rotor positions characterized by each rotor perimeter surface retracting each respective vane toward the respective bore downstream of each respective working fluid outlet simultaneously as the distal end of each respective adjacent upstream lobe moves along each respective bore upstream of each respective working fluid outlet.

13. The rotary engine of claim 12 wherein the fluid handling arrangement comprises a working fluid controller that injects the working fluid at a high energy state into the first and second working fluid inlets, respectively, when the respective rotor has rotated past the neutral rotor position and until the respective rotor has further rotated to a predetermined rotor power stroke position prior to reaching the next neutral rotor position.

14. The rotary engine of claim 13 wherein the working fluid controller selectively varies the amount of energy obtained from the working fluid that is injected into each of the working fluid expansion chambers.

15. The rotary engine of claim 14 wherein the working fluid controller varies the amount of energy from the working fluid in relation to varying one of varying working fluid quality, varying working fluid pressure, and varying working fluid injection duration.

16. A method comprising:
   obtaining a rotary engine having a housing defining a bore, a rotor having a plurality of protuberant lobes that are rotatable against the bore, a plurality of vanes each biased against the rotor as the rotor rotates between neutral rotor positions where each of the plurality of lobes is aligned with a respective vane and a range of power stroke rotor positions between consecutive neutral positions, a steam generator producing steam, a steam controller selectively varying an amount of energy obtained from the steam, and a duration control;
   injecting the steam at a selected energy state determined by the steam controller and for a selected interval determined by the duration control to expand against each of the lobes exerting substantially equivalent torques during an interval when the rotor is at a predetermined power stroke rotor position; and
   exhausting a comparatively low pressure steam downstream, in relation to rotor rotation, of each of the lobes as each respective lobe rotates from the neutral rotor position through the range of power stroke rotor positions where the rotor perimeter surface retracts each vane toward the bore downstream of a respective working fluid outlet simultaneously as the distal end of the respective adjacent lobe moves along the bore upstream of the respective working fluid outlet.

* * * * *